US012037592B2

(12) United States Patent
Loque et al.

(10) Patent No.: US 12,037,592 B2
(45) Date of Patent: Jul. 16, 2024

(54) PLANTS AND METHODS FOR PRODUCING MUCONIC ACID

(71) Applicant: The Regents of the University of California, Oakland, CA (US)

(72) Inventors: Dominique Loque, Vernier (CH); Aymerick Guillaume Eudes, Emeryville, CA (US); Patrick M. Shih, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/796,790

(22) Filed: Feb. 20, 2020

(65) Prior Publication Data

US 2020/0291414 A1 Sep. 17, 2020

Related U.S. Application Data

(60) Provisional application No. 62/808,188, filed on Feb. 20, 2019.

(51) Int. Cl.
*C12N 15/82* (2006.01)

(52) U.S. Cl.
CPC ................................ *C12N 15/8243* (2013.01)

(58) Field of Classification Search
None
See application file for complete search history.

(56) References Cited

U.S. PATENT DOCUMENTS

| | | | | |
|---|---|---|---|---|
| 7,754,943 | B2 * | 7/2010 | Brumbley | C12N 15/8257 800/288 |
| 9,546,387 | B2 * | 1/2017 | Yan | C12Y 402/99021 |
| 9,909,135 | B2 * | 3/2018 | Galili | C12N 15/8255 |
| 2014/0298539 | A1 | 10/2014 | Loque | |
| 2015/0051376 | A1 | 2/2015 | Scheller | |
| 2015/0067920 | A1 * | 3/2015 | Tsai | C12N 9/88 800/288 |
| 2016/0017355 | A1 | 1/2016 | Loque | |
| 2016/0251672 | A1 | 9/2016 | Loque | |

FOREIGN PATENT DOCUMENTS

| | | | |
|---|---|---|---|
| EP | 508909 | A1 | 10/1992 |

OTHER PUBLICATIONS

Morse et al. "Salicylate and catechol levels are maintained in nahG transgenic poplar". Phytochemistry. 68: 2043-2052. (Year: 2007).*
Xue et al. "Constitutively Elevated Salicylic Acid Levels Alter Photosynthesis and Oxidative State but Not Growth in Transgenic Populus". The Plant Cell. 25: 2714-2730 (2013).*
Karp et al. "Alkaline Pretreatment of Switchgrass". ACS Sustainable Chem Eng. 3: 1479-1491. (2015).*
Tohge et al. "Shikimate and phenylalanine biosynthesis in the green lineage". Frontiers in Plant Science: Plant Metabolism and Chemodiversity. (4) (Year: 2013).*
Sonoki, T., Takahashi, K., Sugita, H., Hatamura, M., Azuma, Y., Sato, T., Suzuki, S., Kamimura, N., Masai, E., 2017. Glucose-free cis, cis-muconic acid production via new metabolic designs corresponding to the heterogeneity of lignin. ACS Sustain. Chem. Eng.
Tzin, V., Malitsky, S., Ben Zvi, M.M., Bedair, M., Sumner, L., Aharoni, A., Galili, G., 2012. Expression of a bacterial feedback-insensitive 3-deoxy-D-arabino-heptulosonate 7-phosphate synthase of the shikimate pathway in *Arabidopsis elucidates* potential metabolic bottlenecks between primary and secondary metabolism. New Phytol. 194, 430-439.
Vaillancourt, F.H., Bolin, J.T., Eltis, L.D., 2006. The ins and outs of ring-cleaving dioxygenases. Crit. Rev. Biochem. Mol. Biol. 41, 241-267.
Vega-Sánchez, M.E., Loqué, D., Lao, J., Catena, M., Verhertbruggen, Y., Herter, T., Yang, F., Harholt, J., Eb,ert, B., Baidoo, E.E., Keasling, J.D., Scheller, H.V., Heazlewood, J.L., Ronald, P.C., 2015. Engineering temporal accumulation of a low recalcitrancepolysaccharide leads to increased C6 sugar content in plant cell walls. Plant Biotechnol. J. 13, 903-914.
Widhalm, J.R., Dudareva, N., 2015. A familiar ring to it: biosynthesis of plant benzoic acids. Mol. Plant 8, 83-97.
Wu, W., Dutta, T., Varman, A., Eudes, A., Manalansan, B., Loqué, D., Singh, S., 2017. Lignin valorization: two hybrid biochemical routes for the conversion of polymeric lignin into value-added chemicals. Sci. Rep. 7, 8420.
Xue, L.J., Guo, W., Yuan, Y., Anino, E.O., Nyamdari, B., Wilson, M.C., Frost, C.J., Chen, H.Y., Babst, B.A., Harding, S. A., Tsai, C.J., 2013. Constitutively elevated salicylic acid levels alter photosynthesis and oxidative state but not growth in transgenic Populus. Plant Cell 25, 2714-2730.
Zhang, Y., Butelli, E., Alseekh, S., Tohge, T., Rallapalli, G., Luo, J., Kawar, P.G., Hill, L., Santino, A., Fernie, A.R., Martin, C., 2015. Multi-level engineering facilitates the production of phenylpropanoid compounds in tomato. Nat. Commun. 6, 8635.
Akhtar, T.A., Pichersky, E., 2013. Veratrole biosynthesis in white campion. Plant Physiol. 162, 52-62.
You I-S, Ghosal D & Gunsalus IC (1991) Nucleotide sequence analysis of the Pseudomonas putida PpG7 salicylate hydroxylase gene (nahG) and its 3'-flanking region. Biochem. 30: 1635-1641.
Wu, J., Howe, D. L., and Woodard, R. W. (2003) Thermotoga maritima 3-deoxy-D-arabino-heptulosonate 7-phosphate (DAHP) synthase: the ancestral eubacterial DAHP synthase? J. Biol. Chem. 278, 27525-27531.
Bell-Lelong, D.A., Cusumano, J.C., Meyer, K., Chapple, C., 1997. Cinnamate-4-hydroxylase expression in *Arabidopsis*. Regulation in response to development and the environment. Plant Physiol. 113, 729-738.

(Continued)

*Primary Examiner* — Matthew R Keogh
*Assistant Examiner* — David R Byrnes
(74) *Attorney, Agent, or Firm* — Robin C. Chiang; LAWRENCE BERKELEY NATIONAL LABORATORY

(57) ABSTRACT

The present invention provides for a genetically modified plant or plant cell comprising a nucleic acid encoding one or more heterologous enzymes operatively linked a promoter, wherein one or more heterologous enzymes synthesizes muconic acid (MA).

22 Claims, 18 Drawing Sheets

Specification includes a Sequence Listing.

(56) References Cited

OTHER PUBLICATIONS

Carraher, J.M., Pfennig, T., Rao, R.G., Shanks, B.H., Tessonnier, J.-P., 2017. Cis,cis-Muconic acid isomerization and catalytic conversion to biobased cyclic-C6-1,4-diacid monomers. Green Chem. 19, 3042-3050.
Eudes, A., Sathitsuksanoh, N., Baidoo, E.E., George, A., Liang, Y., Yang, F., Singh, S., Keasling, J.D., Simmons, B.A., Loqué, D., 2015. Expression of a bacterial 3-dehydroshikimate dehydratase reduces lignin content and improves biomass saccharification efficiency. Plant Biotechnol. J. 13, 1241-1250.
Eudes, A., Pereira, J.H., Yogiswara, S., Wang, G., Teixeira Benites, V., Baidoo, E.E., Lee, T.S., Adams, P.D., Keasling, J.D., Loqué, D., 2016. Exploiting the substrate promiscuity of hydroxycinnamoyl-CoA: shikimate hydroxycinnamoyl transferase to reduce lignin. Plant Cell Physiol. 57, 568-579.
Friedrich, L., Vernooij, B., Gaffney, T., Morse, A., Ryals, J., 1995. Characterization of tobacco plants expressing a bacterial salicylate hydroxylase gene. Plant Mol. Biol. 29, 959-968.
Gallego-Giraldo, L., Escamilla-Trevino, L., Jackson, L.A., Dixon, R.A., 2011. Salicylic acid mediates the reduced growth of lignin down-regulated plants. Proc. Natl. Acad. Sci. U S A. 108, 20814-20819.
Johnson, C.W., Salvachúa, D., Khanna, P., Smith, H., Peterson, D.J., Beckham, G.T., 2016. Enhancing muconic acid production from glucose and lignin-derived aromatic compounds via increased protocatechuate decarboxylase activity. Metab. Eng. Commun. 3, 111-119.
Johnson, C.W., Abraham, P.E., Linger, J.G., Khanna, P., Hettich, R.L., Beckham, G.T., 2017. Eliminating a global regulator of carbon catabolite repression enhances the conversion of aromatic lignin monomers to muconate in Pseudomonas putida KT2440. Metab. Eng. Commun. 5, 19-25.
Karp, E.M., Donohoe, B.S., O'Brien, M.H., Ciesielski, P.N., Mittal, A., Biddy, M.J., Beckham, G.T., 2014. Alkaline pretreatment of corn stover: bench-scale fractionation and stream characterization. ACS Sustain. Chem. Eng. 2, 1481-1491.
Last, R.L., Fink, G.R., 1988. Tryptophan-requiring mutants of the plant *Arabidopsis thaliana*. Science 240, 305-310.
Lindroth, R.L., Hwang, S.Y., 1996. Diversity, redundancy and multiplicity in chemical defense systems of aspen. Recent Adv. Phytochem. 30, 25-56.
Maeda, H., Dudareva, N., 2012. The shikimate pathway and aromatic amino acid biosynthesis in plants. Annu. Rev. Plant Biol. 63, 73-105.
Matthiesen, J.E., Carraher, J.M., Vasiliu, M., Dixon, D.A., Tessonnier, J.-P., 2016. Electrochemical conversion of muconic acid to biobased diacid monomers. ACS Sustain. Chem. Eng. 4, 3575-3585.
Serrano, M., Wang, B., Aryal, B., Garcion, C., Abou-Mansour, E., Heck, S., Geisler, M., Mauch, F., Nawrath, C., Métraux, J.P., 2013. Export of salicylic acid from the chloroplast requires the multidrug and toxin extrusion-like transporter EDS5. Plant Physiol. 162, 1815-1821.
Shih, P.M., Vuu, K., Eudes, A., Loqué D., 2016a. Bioproduction of muconic acid in plants. International Conference on Plant Synthetic Biology and Bioengineering, Miami Beach, FL. Dec. 16-18.
Shih, P.M., Liang, Y., Loqué, D., 2016b. Biotechnology and synthetic biology approaches for metabolic engineering of bioenergy crops. Plant J. 87, 103-117.
Eudes, Aymerick, et al. "Production of Muconic Acid in Plants." Metabolic Engineering, vol. 46, 2018, pp. 13-19., doi:10.1016/j.ymben.2018.02.002.

* cited by examiner

PLANTS AND METHODS FOR PRODUCING MUCONIC ACID

CROSS-REFERENCE TO RELATED APPLICATIONS

The application claims priority to U.S. Provisional Patent Application Ser. No. 62/808,188, filed Feb. 20, 2019, which is herein incorporated by reference in its entirety.

STATEMENT OF GOVERNMENTAL SUPPORT

This invention was made with government support under Contract No. DE-AC02-05CH11231 awarded by the United States Department of Energy. The government has certain rights in the invention.

FIELD OF THE INVENTION

This invention relates generally to producing muconic acid.

BACKGROUND OF THE INVENTION

Muconic acid (MA) is a platform chemical that serves as a precursor for the synthesis of products such as adipic acid, terephthalic acid, and caprolactam which are widely used in the nylon and thermoplastic polymer industries. Current processes for the manufacturing of MA or its derivatives mainly rely on non-renewable petroleum-based chemicals. Such processes are not sustainable and eco-friendly since they require a high energy input and yield large quantities of toxic by-products (Xie et al., 2014).

As an alternative, the biological production of MA using engineered microorganisms and inexpensive carbohydrate feedstocks has received increasing attention over the past 20 years (Xie et al., 2014). Most of the established biological routes consist in the production catechol and its subsequent conversion into MA by ring-cleaving catechol 1,2-dioxygenase (Vaillancourt et al., 2006). All these routes exploit the intrinsic shikimate pathway for the biosynthesis of catechol precursors such as protocatechuate, anthranilate, salicylic acid (SA), and 2,3-dihydroxybenzoic acid (Kruyer and Peralta-Yahya, 2017). Recently, MA biosynthetic pathways have been implemented in various microbial strains capable of growing in the presence of aromatics derived from lignocellulosic biomass. These include engineered strains of *Escherichia coli* (Sonoki et al., 2014, Wu et al., 2017), *Amycolatopsis* sp. (Barton et al., 2017), *Pseudomonas* sp. (Vardon et al., 2015, Johnson et al., 2016, Johnson et al., 2017, Sonoki et al., 2017), and *Sphingobium* sp. (Sonoki et al., 2017).

In addition to microbial synthesis, the metabolic engineering of photosynthetic organisms like plants also provides a sustainable approach for the production of valuable metabolites and materials (Börnke and Broer, 2010, Farré et al., 2014). These chemicals, when produced in engineered bioenergy and oilseed crops, represent value-added renewable co-products on top of the lignocellulose and seed oil used to generate energy (Snell et al., 2015). Because plants are autotrophs able to capture solar energy, they represent an attractive chassis for implementing de novo metabolic pathways for cost-effective production of important chemicals (Yuan and Grotewold, 2015).

SUMMARY OF THE INVENTION

The present invention provides a genetically modified plant or plant cell comprising a nucleic acid encoding one or more heterologous enzymes operatively linked a promoter, wherein one or more heterologous enzymes synthesizes muconic acid (MA) from a salicylic acid (SA). The genetically modified host cell can comprise one of the enzymatic pathways necessary for producing a muconic acid described herein.

In some embodiments, the genetically modified plant or plant cell comprises nucleic acid encoding one or more heterologous enzymes wherein the plant cell or transgenic plant is capable of producing a muconic acid. The genetically modified plant cell or transgenic plant can comprise one of the enzymatic pathways for producing a muconic acid described herein, such as starting with DAHP, shikimate or chorismate as a precursor.

The present invention provides for a method for producing a muconic acid comprising: (a) optionally genetically modifying a plant cell or transgenic plant to produce a genetically modified plant cell of the present invention, (b) growing or culturing the genetically modified plant cell or transgenic plant to produce a muconic acid, (c) optionally pretreating the plant cell or transgenic plant, and (d) optionally converting the muconic acid into an adipic acid, terephthalic acid, and/or caprolactam.

In some embodiments, the heterologous enzymes are salicylate hydroxylase and/or catechol 1,2-dioxygenase. In some embodiments, the salicylate hydroxylase (NahG) is a bacterial or *Pseudomonas* salicylate hydroxylase (NahG). In some embodiments, the salicylate hydroxylase (NahG) comprises an amino acid sequence that is at least 70%, 80%, 90%, 95%, or 99% identical to the amino acid sequence of *Pseudomonas* salicylate hydroxylase (NahG), and comprises the enzymatic activity of salicylate hydroxylase (NahG). In some embodiments, the salicylate hydroxylase comprises one or both of the following ADP binding site amino acid sequences: GXGXXG (SEQ ID NO:5) and/or HGRXXLXGD (SEQ ID NO:6), wherein X is any naturally occurring amino acid. In some embodiments, the salicylate hydroxylase comprises one or more of the conserved amino acid sequences described in You et al., *Biochem.* 30:1635-1641 (1991).

The amino acid sequence of *Pseudomonas putida* salicylate hydroxylase (NahG) comprises:

```
                                                  (SEQ ID NO: 1)
        10          20          30          40          50
MKNNKLGLRI  GIVGGGISGV  ALALELCRYS  HIQVQLFEAA  PAFGEVGAGV

        60          70          80          90         100
SFGPNAVRAI  VGLGLGEAYL  QVADRTSEPW  EDVWFEWRRG  SDASYLGATI

       110         120         130         140         150
APGVGQSSVH  RADFIDALVT  HLPEGIAQFG  KRATQVEQQG  GEVQVLFTDG
```

-continued

```
       160        170        180        190        200
TEYRCDLLIG ADGIKSALRS HVLEGQGLAP QVPRFSGTCA YRGMVDSLHL

       210        220        230        240        250
REAYRAHGID EHLVDVPQMY LGLDGHILTF PVRNGGIINV VAFISDRSEP

       260        270        280        290        300
KPTWPADAPW VREASQREML DAFAGWGDAA RALLECIPAP TLWALHDLAE

       310        320        330        340        350
LPGYVHGRVV LIGDAAHAML PHQGAGAGQG LEDAYFLARL LGDTQADAGN

       360        370        380        390        400
LAELLEAYDD LRRPRACRVQ QTSWETGELY ELRDPVVGAN EQLLGENLAT

       410        420        430
RFDWLWNHDL DTDLAEARAR LGWEHGGGGA LRQG
```

In some embodiments, the catechol 1,2-dioxygenase (CatA) is a bacterial or *Pseudomonas* catechol 1,2-dioxygenase (CatA). In some embodiments, the catechol 1,2-dioxygenase (CatA) comprises an amino acid sequence that is at least 70%, 80%, 90%, 95%, or 99% identical to the amino acid sequence of *Pseudomonas* catechol 1,2-dioxygenase (CatA), and comprising the enzymatic activity of catechol 1,2-dioxygenase (CatA). In some embodiments, the catechol 1,2-dioxygenase comprises one or more of the following amino acid residues acting as Fe ligands, or associated with thereof: Y at position 163 of SEQ ID NO:2, Y at position 197 of SEQ ID NO:2, and/or RPAHXH (SEQ ID NO:7), wherein X is any naturally occurring amino acid.

The amino acid sequence of *Pseudomonas putida* catechol 1,2-dioxygenase (CatA) comprises:

```
                                                  (SEQ ID NO: 2)
        10         20         30         40         50
MTVKISHTAD IQAFFNRVAG LDHAEGNPRF KQIILRVLQD TARLIEDLEI

        60         70         80         90        100
TEDEFWHAVD YLNRLGGRNE AGLLAAGLGI EHFLDLLQDA KDAEAGLGGG

       110        120        130        140        150
TPRTIEGPLY VAGAPLAQGE ARMDDGTDPG VVMFLQGQVF DADGKPLAGA

       160        170        180        190        200
TVDLWHANTQ GTYSYFDSTQ SEFNLRRRII TDAEGRYRAR SIVPSGYGCD

       210        220        230        240        250
PQGPTQECLD LLGRHGQRPA HVHFFISAPG HRHLTTQINF AGDKYLWDDF

       260        270        280        290        300
AYATRDGLIG ELRFVEDAAA ARDRGVQGER FAELSFDFRL QGAKSPDAEA

       310
RSHRPRALQE G
```

In some embodiments, the genetically modified plant or plant cell endogenously produces salicylic acid (SA). In some embodiments, the genetically modified plant or plant cell further comprises one or more enzymes that in the pathway that converts PEP and/or E4P into SA, such that the genetically modified plant or plant cell produces SA. In some embodiments, the one or more enzymes that in the pathway that converts PEP and/or E4P into SA are heterologous to the genetically modified plant or plant cell.

In some embodiments, the genetically modified plant or plant cell further comprises bifunctional ISOCHA synthase/ISOCHA pyruvate lyase (Irp9) and/or feedback-resistant DAHP synthase (L175Q) (AroG*). In some embodiments, the bifunctional ISOCHA synthase/ISOCHA pyruvate lyase (Irp9) is bacterial or *Yersinia enterocolitica* bifunctional ISOCHA synthase/ISOCHA pyruvate lyase (Irp9). In some embodiments, the feedback-resistant DAHP synthase (L175Q) (AroG*) is bacterial or *E. coli* DAHP synthase (AroG) that has a L175Q mutation which causes the AroG to be feedback resistant.

In some embodiments, the bifunctional ISOCHA synthase/ISOCHA pyruvate lyase (Irp9) comprises an amino acid sequence that is at least 70%, 80%, 90%, 95%, or 99% identical to the amino acid sequence of *Yersinia enterocolitica* bifunctional ISOCHA synthase/ISOCHA pyruvate lyase (Irp9), and comprises the enzymatic activity of bifunctional ISOCHA synthase/ISOCHA pyruvate lyase (Irp9). In some embodiments, the bifunctional ISOCHA synthase/ISOCHA pyruvate lyase comprises the amino acid sequence from position 173 to position 424 of SEQ ID NO:3 which comprises a chorismate binding domain.

The amino acid sequence of *Yersinia enterocolitica* bifunctional ISOCHA synthase/ISOCHA pyruvate lyase (Irp9) comprises:

```
                                                        (SEQ ID NO: 3)
        10         20         30         40         50
MKISEFLHLA LPEEQWLPTI SGVLRQFAEE ECYVYERPPC WYLGKGCQAR

        60         70         80         90        100
LHINADGTQA TFIDDAGEQK WAVDSIADCA RRFMAHPQVK GRRVYGQVGF

       110        120        130        140        150
NFAAHARGIA FNAGEWPLLT LTVPREELIF EKGNVTVYAD SADGCRRLCE

       160        170        180        190        200
WVKEASTTTQ NAPLAVDTAL NGEAYKQQVA RAVAEIRRGE YVKVIVSRAI

       210        220        230        240        250
PLPSRIDMPA TLLYGRQANT PVRSFMFRQE GREALGFSPE LVMSVTGNKV

       260        270        280        290        300
VTEPLAGTRD RMGNPEHNKA KEAELLHDSK EVLEHILSVK EAIAELEAVC

       310        320        330        340        350
LPGSVVVEDL MSVRQRGSVQ HLGSGVSGQL AENKDAWDAF TVLFPSITAS

       360        370        380        390        400
GIPKNAALNA IMQIEKTPRE LYSGAILLLD DTRFDAALVL RSVFQDSQRC

       410        420        430
WIQAGAGIIA QSTPERELTE TREKLASIAP YLMV
```

In some embodiments, the feedback-resistant DAHP synthase (L175Q) (AroG*) comprises an amino acid sequence that is at least 70%, 80%, 90%, 95%, or 99% identical to the amino acid sequence of *E. coli* DAHP synthase (AroG) and a glutamine at the position corresponding to position 175 of the *E. coli* DAHP synthase, and comprises the enzymatic activity of feedback-resistant DAHP synthase (L175Q) (AroG*). In some embodiments, the DAHP synthase (AroG) comprises one or more of the following amino acid residues acting as metal-binding sites: C at position 61 of SEQ ID NO:4, H at position 268 of SEQ ID NO:4, E at position 302 of SEQ ID NO:4, and/or D at position 326 of SEQ ID NO:4, and/or any conserved amino acid residues disclosed in Wu et al., *J. Biol. Chem.* 278(30):27525-27531 (2003).

The amino acid sequence of *E. coli* DAHP synthase (AroG) comprises:

```
                                                        (SEQ ID NO: 4)
        10         20         30         40         50
MNYQNDDLRI KEIKELLPPV ALLEKFPATE NAANTVAHAR KAIHKILKGN

        60         70         80         90        100
DDRLLVVIGP CSIHDPVAAK EYATRLLALR EELKDELEIV MRVYFEKPRT

       110        120        130        140        150
TVGWKGLIND PHMDNSFQIN DGLRIARKLL LDINDSGLPA AGEFLDMITP

       160        170        180        190        200
QYLADLMSWG AIGARTTESQ VHRELASGLS CPVGFKNGTD GTIKVAIDAI

       210        220        230        240        250
NAAGAPHCFL SVTKWGHSAI VNTSGNGDCH IILRGGKEPN YSAKHVAEVK

       260        270        280        290        300
EGLNKAGLPA QVMIDFSHAN SSKQFKKQMD VCADVCQQIA GGEKAIIGVM

       310        320        330        340        350
VESHLVEGNQ SLESGEPLAY GKSITDACIG WEDTDALLRQ LANAVKARRG
```

In some embodiments, the genetically modified plant or plant cell endogenously produces chorismate (CHA).

In some embodiments, the genetically modified plant or plant cell comprising a nucleic acid encoding the following heterologous enzymes: NahG, CatA, optionally Irp9, and optionally AroG*, each operatively linked to a promoter capable of expressing each enzyme in the genetically modified plant or plant cell.

In some embodiments, each enzyme is expressed in, or expressed and transport to, a plastid in the genetically modified plant or plant cell.

In some embodiments, the promoter is tissue-specific.

The present invention provides for a plant capable of producing a diversity of metabolic pathways for the production of muconic acid (MA). There are five main pathways starting directly from or depending on the aromatic amino acid biosynthesis pathway. The latter pathway consumes about 30% of photosynthetically fixed carbon meaning that it offers great potentials for large production at low cost of target products, such as MA.

The first pathway starts from 3 dihydroshikimate that get converted into protochatechuate by a plastid localized 3-hydroshikimate dehydratase (3-DHSDH; Eudes et al, 2015), then into catechol by a protocatechuate decarboxylase (PDC), and finally into MA by a catechol dioxygenase (CDO).

The second pathway starts from chorismate to produce also protochatechuate (Eudes et al., 2016) by the co-expression two plastid targeted enzymes: chorismate pyruvate-lyase (such as, *E. coli* ubiC) and p-hydroxybenzoate 3-monooxygenase (such as, *Pseudomonas aeruginosa* pobA). Then, protochatechuate can be converted into MA as described herein.

The third pathway uses chorismate to produce the 2,3 dihydroxybenzoate by targeting to plastids a cluster of three proteins: entC (isochorimate synthase), entB (isochorismatase) and entA (2,3 dihydroxybenzoate synthase). Then MA is produced from the decarboxylation of 2,3 dihydroxybenzoate by benzoate decarboxylase (BDC) to produce catechol followed by ring opening with a catechol dioxygenase (CDO).

The fourth pathway starts from anthranilate that is converted in plastid into catechol by the expression of a multicomponent aromatic ring-dihydroxylating enzyme complex (antABC). Then the catechol is converted into MA by a catechol dioxygenase (CDO).

The fifth pathway uses salicylic acid that is mainly derived from chorismate. Salicylic acid gets converted into catechol by salicylate 1-monoxygenase (SMO) followed by ring opening with a catechol dioxygenase (CDO) to produce MA.

Flux through several of these pathways can be boosted to enhance yield of the final product MA (booster pathways). In some embodiments, carbon entry through the aromatic amino acid biosynthesis pathway can be enhanced by the expression of an insensitive phospho-2-dehydro-3-deoxyheptonate aldolase (AroG; first enzyme of the pathway); salicylic production derived from chorismate can be increased by the expression of bifunctional salicylate synthase (irp9) or both enzymes; isochorismate synthase (ICS) and isochorismate pyruvate lyase (IPL); anthranilate production could be enhanced by the expression of tryptophan insensitive anthranilate synthase (trp5) to increase flux from chorismate to anthranilate.

The present invention provides for transgenic plants transformed with each or stacks of these artificial MA pathways with or without booster pathways, will produce diverse quantities of muconic acid in their tissues. The bioproduction of muconic acid is of interest because of its potential use as a platform chemical for the production of other valuable bioplastics, such as nylon-6,6, polyurethane, and polyethylene terephthalate (PET).

Bioproduction of muconic acid using fermenting microbes is being developed, but bioproduction in plants has never before been described nor demonstrated. The present invention which uses plants as factories is more eco-friendly and sustainable. Herein is described the expression of bacterial CDO in plastids which results in plants producing muconic acid, a metabolite that in nature is not found in plants. Two CDOs are screened: CDO from *Pseudomonas putita* is more efficient than CDO from *Acinetobacter radioresistens*. Since most pathways go through the ring opening of catechol, several CDO enzymes (same enzyme differently codon optimized, or from different species) can be stacked and co-expressed. In some embodiments, the nucleotide sequence encoding each heterologous enzyme is codon optimized specifically for the plant or plant cell.

In some embodiments, the promoter is a CER1, CER2, CER3, CER4, CER5, CER6, CER10, WSD1, Mah1, WBC11, KCS1, KCS2, FATB, LACS1, LACS2, CYP864A, CYP86A7, CYP86A5, KCS10, or KCS5 promoter. In some embodiments, the tissue-specific promoter are as described herein. In embodiments, the fiber-specific promoter is an NST, NST1, NST2, NST3, or LAC17 promoter. In some embodiments, the vessel-specific promoter is a VND1, VND2, VND3, VND4, VND5, VND6, VND7, VNI2, REF4, or RFR1 promoter. In some embodiments, the secondary cell wall-specific promoter is an IRX1, IRX3, IRX5, IRX8, IRX9, IRX14, IRX7, IRX10, GAUT13, GAUT14, or CESA4 promoter. Suitable tissue-specific secondary wall promoters, and other transcription factors, promoters, regulatory systems, and the like, suitable for this present invention are taught in U.S. Patent Application Pub. Nos. 2014/0298539, 2015/0051376, 2016/0017355, and 2016/0251672.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1:
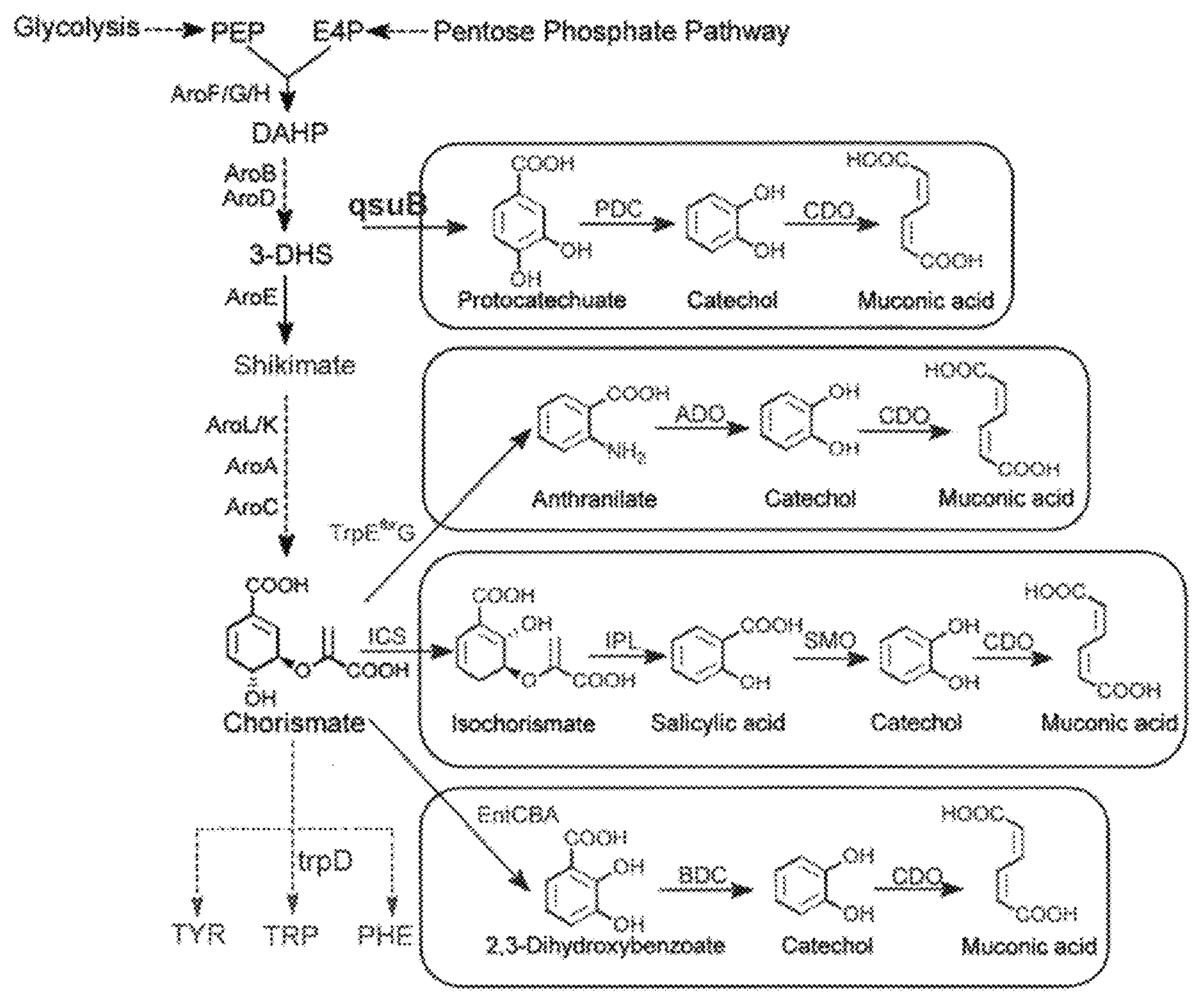
FIG. 1. The various pathways for producing muconic acid.

The foregoing aspects and others will be readily appreciated by the skilled artisan from the following description of illustrative embodiments when read in conjunction with the accompanying drawings.

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The term "about" refers to a value including 10% more than the stated value and 10% less than the stated value.

Useful nucleotide sequences for use in expressing the heterologous enzymes are described:

attB1-schl1-irp9-attB2: Codon-optimized nucleotide sequence encoding Irp9 from *Yersinia enterocolitica* (in red, GenBank accession number CAB46570.1) preceded with a plastid targeting signal (in green, schl1) and flanked with Gateway attB1 (5'-end) and attB2 (3'-end) recombination sites (in black):

```
                                             (SEQ ID NO: 8)
ACAAGTTTGTACAAAAAAGCAGGCTTCATGGCATCAACAGCATTATCATC
CGCTATCGTGGGAACATCATTCATTAGGAGGAGTCCAGCACCAATCAGTC
TTAGATCATTACCTTCTGCAAACACACAATCACTTTTCGGTTTCAAATCT
GGAACCGCTAGAGGTGGAAGGGTTACAGCTATGGCAACCTATAAGGTTAT
GAAAATCAGTGAATTCTTGCATTTGGCACTTCCAGAAGAGCAATGGTTGC
CTACTATCTCCGGTGTTTTAAGACAGTTCGCTGAAGAGGAATGTTATGTG
TACGAAAGACCACCTTGTTGGTACTTAGGTAAAGGATGCCAAGCTAGACT
TCACATCAACGCAGATGGTACCCAAGCTACTTTTATAGATGACGCAGGAG
AACAGAAATGGGCTGTTGATTCTATTGCAGACTGCGCTAGAAGGTTCATG
GCACATCCACAAGTTAAGGGTAGAAGGGTTTATGGTCAAGTGGGTTTTAA
TTTCGCTGCACACGCTAGAGGTATAGCTTTTAATGCTGGAGAATGGCCAT
TGTTAACTCTTACAGTTCCTAGAGAGGAATTGATTTTCGAGAAGGGTAAT
GTGACTGTTTACGCAGATTCTGCTGACGGATGTAGAAGGTTGTGCGAGTG
GGTTAAGGAAGCTTCAACTACAACCCAAAATGCACCTCTTGCTGTTGATA
CAGCATTGAACGGTGAAGCTTATAAGCAACAGGTTGCTAGAGCAGTGGCT
GAGATCAGAAGGGGAGAATACGTGAAGGTTATCGTGTCTAGAGCTATACC
ATTGCCTTCAAGGATAGATATGCCAGCAACCCTTTTGTATGGTAGACAAG
CTAATACTCCTGTTAGGTCTTTTATGTTCAGACAGGAGGGTAGGGAAGCA
TTAGGATTCTCTCCAGAGCTTGTTATGTCAGTGACTGGAAACAAAGTTGT
GACAGAACCATTAGCTGGTACCAGAGATAGGATGGGAAATCCTGAGCATA
ACAAAGCAAAGGAGGCTGAATTACTTCATGACAGTAAAGAGGTTTTAGAA
CACATACTTTCCGTGAAGGAAGCAATTGCTGAGTTGGAAGCTGTTTGTTT
ACCTGGTTCAGTTGTGGTTGAAGATTTGATGAGTGTTAGACAAAGGGGTT
CCGTGCAGCACTTGGGTTCTGGAGTTTCAGGACAATTAGCTGAAAACAAG
GATGCATGGGACGCTTTTACTGTTCTTTTCCCAAGTATTACAGCATCCGG
TATCCCTAAAAATGCTGCACTTAACGCTATAATGCAAATTGAGAAGACTC
CAAGAGAATTGTACAGTGGAGCTATATTGCTTCTTGATGACACAAGATTC
GATGCTGCATTGGTTTTAAGGAGTGTGTTCCAAGACTCCCAGAGATGCTG
GATCCAAGCAGGTGCTGGAATTATCGCTCAGTCAACACCTGAGAGAGAGT
TGACTGAGACTAGGGAGAAATTAGCATCAATCGCACCTTACCTTATGGTT
TGAGACCCAGCTTTCTTGTACAAAGTGGTC
```

attB4r-tG7-pCCoAOMT-attB3r: Sequence containing the tg7 terminator from *A. tumefaciens* followed by the CCoA-OMT1 promoter from *A. thaliana* (in black) containing an AvrII restriction site (in red) in its 3'-end and flanked with the Gateway attB4R (5'-end) and attB3R (3'-end) recombination sites (in blue):

```
                                             (SEQ ID NO: 9)
GACAACTTTTCTATACAAAGTTGACTGACTAACTAGGATGAGCTAAGCTA
GCTATATCATCAATTTATGTATTACACATAATATCGCACTCAGTCTTTCA
TCTACGGCAATGTACCAGCTGATATAATCAGTTATTGAAATATTTCTGAA
TTTAAACTTGCATCAATAAATTTATGTTTTTGCTTGGACTATAATACCTG
ACTTGTTATTTTATCAATAAATATTTAAACTATATTTCTTTCAAGATGGG
AATTAACATCTACAAATTGCCTTTTCTTATCGACCATGTACCCCGGGTAC
CAAGCTTCTCGAGAGCAGTGGATGAGGGAAGAGAGGATTAAGAGGCGTAG
AGATTACATGTGATGAATGATACTATCTTTTCTTACAAACACATTTTCGT
GTAATTAAAATTTAATTTGGTTCCAAAGATTTTAATCAAAAGAAGTTTGG
TAAATTGAAACAGGCAGACATAATTTATTGTAAAGAGTTTTTATTTATTT
ATTCATGACGTTGCTTGATGGTGCTTTACCAATTTTCTTCTCCTACGTTA
GATTTTTTTCACTTTTTTTTTTGGTGTTTGTAATAAATGTGAAAAATGGA
CCGTTTAAAAACTTAAAGACGTTTGATTACTATATAAAGTAATTGTTTAT
AATAGAAAGTTAATTGAGACGTGAAATGGTATAATATTATTGTGTAACAG
TTGTGTACACGTAGCTCTCATGCAGTTTTAGTGGACCCATATGGCTTGAC
TTGTATTCTGTTTTTGGGCTATTAAAGTCCAAAACAGAGACCCCTCTCAA
GCCCTTCCTATTAATCCATCTAGCTAATAGAAACTATAAACGTGTCCTCT
CTCTCAATTAAATAAGCTAGAAACATACTCAACCATTCGCATTACGCACT
TCATAGCGGTAGGTTTAGATTTGTCTAAAATACTTAAAAAAATTTTTGTC
TAAGTTGTTGTCCGTTACAAAGTTTTTTTCTTTGTGACAACTTGACAACA
TTGACAAATAGAAAAATAAATTTCGATGAAACCTATGAAATGGGCTATGG
CCCAACTAAAAAGAGTGGGAAATTAAAGATGGGATGGTTCAAGTGTATAC
TTCGAACTTCCGACATTAGGGTCAAAGGATTTTTAAAAGGCAACCATTTG
TTCCACTTTCTCGAACAAAAACGAGCCATTTATTAATATATAGTACGGCT
GAATTGGTTTTGTTCGTCATTGTGTAAACACAAAGTCATTCGAATTATGT
TAGGGTCCGTTGATAATATAGACGGCCCATCCCACGCACATATTAAGTGT
TCAACTCCATAGAATATCATATGGGACACTGTTTTTAATTTATAATCACC
ATTTAAAATGTTTAAATGTTTATGCAAATTGGATGGCTTCTTCACACAAC
ATTTATTTATTGGCCTTTCATTCCATCAAAGTAAAATAGCTTTTCAAATA
CATTATACTCTATACTCCTATACATGTAAATAACCATATGCATATATATT
TTTTTCAAATATAGGTCAACGCCATTTAATATAATTTTAAAAAAATTTGT
TCGGAAAATATCACATTTCTTTCACTAGACAAGCCTTGTTACCACACAAT
GTATCAATATGATCTAAAGGGCAAACGAAAGATCCTGACATGAAACGTTT
AATTCTCATTTTCTCCAAATTTTATTTTTTATGTGAAGTAGATAAATTAG
TATATATATATATATACCAAACTAGTGTGTTATGTTATGGCAAATGTTAT
ATCAATTCGAAGGTTCCGCTATTGCAATATTCATTAATTTTTTCATACCA
ATACTATTTTTCTTTCTCTTTTATTTTGTTTTTTAATAAATAAAAGAAAT
TAAGGATGATTAGTAAGGAAGTCGCCTACCAAGAGATTCACCTACCACGG
```

-continued

```
TACACTTCAACACCGAAGCAGAGTTGTTGAATCCACTTTTTATTCCCTTC
TCTAATCTCTACTCACCAAGTCTCCACTTTTTTTTCTCTTTATTATATAC
ATTTAAATTATTTAATATACGCCAACTACATACATATCCAGTGTAATTTC
TCGTTACGTCACACCCCTTTCGTAATCGTCTAATTTCAGAAAAATATCCA
GAGGTTTAAATACATATTCCCATCATTAAATCTAGACATAAACACATCAT
ACTCACAAAATTTGGCAGCAAACAGTTACTACAGACCCATAAATGAAAAA
ACGTATTCACTTGTTTTCAATTTTCACATAACCACTTCCCTGAGTTTGGT
CTCAATTTGATTGCCCCGCCGAGGCATTACTACGCCAAGTGCGATTAAGG
TCCCATACAGTGTAACGGGACCCACTATAAGACAGCGACCGACCAATTGC
GTGTTAGGAGAGTTTCACCAACCCCGGACCGGTTTTTACCGGATATAACA
GAACCGGTACGAACCGGTCTCATTATCTTCCATCTTCTTTATATAGACCT
CATGCCATGTGTGTGACTCACCAAGAAAAACACAATCGTTTAATCTCACC
CAAGAAGACAAAAACACAGAGAGAGAAAGAGAGAGAAACAACTTTGTATA
ATAAAGTTGTC
```

attB3-schl2-aroG-attB2: Codon-optimized nucleotide sequence encoding feedback-insensitive AroG (L175Q) from *E. coli* (in red, NCBI Reference Sequence: WP_032246946.1) preceded with a plastid targeting signal (in green, schl2) and flanked with Gateway attB3 (5'-end) and attB2 (3'-end) recombination sites (in black):

```
ACAACTTTGTATAATAAAGTTGGCCATGGCTTCTATGATATCCTCTTCAG
CTGTGACTACAGTCAGCCGTGCTTCTACGGTGCAATCGGCCGCGGTGGCT
CCATTCGGCGGCCTCAAATCCATGACTGGATTCCCAGTTAAGAAGGTCAA
CACTGACATTACTTCCATTACAAGCAATGGTGGAAGAGTAAAGTGCATGC
AGATGAATTACCAGAACGATGACTTAAGAATCAAAGAAATTAAAGAGTTG
TTACCACCTGTGGCTCTTTTGGAAAAATTCCCAGCAACTGAGAATGCTGC
AAACACAGTTGCTCATGCAAGAAAGGCTATTCACAAAATCTTGAAGGGTA
ATGATGACAGGTTACTTGTTGTGATCGGACCATGCTCAATACATGATCCT
CTTGCTGCAAAGGAATACGCTACTAGATTGCTTGCATTGAGGGAAGAGTT
AAAGGATGAACTTGAGATTGTTATGAGAGTGTACTTCGAGAAACCAAGGA
CCACTGTTGGTTGGAAGGGACTTATCAATGATCCTCACATGGACAACTCC
TTCCAAATTAATGATGGTTTGAGAATCGCTAGGAAACTTTTGCTTGATAT
TAACGACTCAGGTTTGCCAGCTGCAGGAGAATTTTTAGATATGATCACAC
CTCAGTACTTAGCTGACCTTATGTGATGGGGTGCTATAGGAGCAAGAACA
ACCGAAAGTCAAGTTCATAGGGAGCAGGCTTCCGGTTTGTCTTGTCCAGT
GGGATTCAAAAATGGTACTGATGGAACAATTAAGGTTGCTATAGACGCAA
TTAACGCTGCAGGTGCTCCTCATTGTTTTCTTTCTGTTACAAAATGGGGA
CACTCAGCAATCGTGAATACCAGTGGTAACGGAGATTGCCATATTATCTT
GAGAGGTGGAAAAGAACCAAATTATTCAGCTAAGCACGTTGCAGAAGTGA
AAGAGGGTTTGAACAAGGCTGGATTACCTGCACAAGTTATGATCGATTTC
TCTCATGCTAACTCCTCTAAGCAATTCAAGAAACAGATGGATGTTTGTGC
```

-continued

```
TGACGTGTGCCAACAGATCGCTGGTGGAGAAAAGGCTATTATTGGTGTTA
TGGTGGAAAGTCACTTAGTTGAGGGAAATCAATCATTAGAAAGTGGAGAG
CCTCTTGCTTACGGAAAATCTATTACCGATGCATGCATCGGTTGGGAAGA
TACTGACGCTCTTTTGAGACAGTTGGCTAACGCAGTTAAGGCAAGAAGGG
GTTGAGACCCAGCTTTCTTGTACAAAGTGGTC
```

attB1-schl3-catA-attB4: Codon-optimized nucleotide sequence encoding CatA from *Pseudomonas* (in red, NCBI Reference Sequence: WP_010954549.1) preceded with a plastid targeting signal (in green, schl3) and flanked with Gateway attB1 (5'-end) and attB4 (3'-end) recombination sites (in black):

```
                                          (SEQ ID NO: 10)
ACAAGTTTGTACAAAAAAGCAGGCTTCATGGCGAGTATCTCCAGCAGCGT
TGCGACAGTGAGCAGAACAGCACCGGCACAAGCGAATATGGTTGCACCGT
TTACGGGATTGAAAAGTAATGCTGCGTTTCCAACCACTAAAAAGGCCAAT
GATTTCTCGACACTGCCGTCCAACGGTGGCCGTGTTCAGTGTATGCAAGT
GTGGCCGGCTTATGGAAACAAAAAGTTTGAAACTCTGTCTTACCTTCCGC
CTTTGTCAACAATGGCGCCTACGGTCATGATGGCATCTTCAGCAACCGCC
GTGGCTCCATTCCAGGGTCTGAAAAGCACTGCTAGTCTTCCTGTGGCTCG
CCGTTCTTCCCGCTCGCTTGGTAATGTTTCTAATGGAGGTCCTATCAGAT
GCATGCAGATGACCGTGAAAATCTCCCACACTGCTGACATACAGGCATTC
TTTAACAGAGTTGCTGGATTAGACCACGCTGAAGGTAACCCAAGGTTCAA
GCAAATTATCTTGAGAGTTCTTCAGGATACTGCTAGGTTAATCGAAGATC
TTGAGATAACAGAAGACGAGTTCTGGCATGCTGTGGATTATCTTAATAGA
TTGGGTGGAAGGAACGAAGCAGGTTTGTTAGCTGCAGGACTTGGTATAGA
GCACTTTTTGGATCTTTTGCAAGATGCTAAAGACGCTGAAGCAGGTTTGG
GTGGTGGTACTCCAAGAACTATTGAGGGACCTTTGTATGTTGCTGGTGCA
CCATTAGCTCAAGGAGAAGCAAGGATGGATGACGGAACAGATCCTGGTGT
TGTGATGTTTTTACAGGGTCAGGTTTTCGATGCTGACGGAAAGCCACTTG
CTGGTGCAACCGTGGATTTGTGGCATGCTAACACACAAGGTACTTATTCT
TACTTCGATTCTACCCAGTCAGAATTCAATTTGAGAAGAAGAATTATTAC
TGATGCTGAGGGAAGGTATAGAGCAAGGAGTATCGTTCCTTCCGGATACG
GTTGTGATCCACAAGGACCTACTCAGGAATGCTTAGACTTACTTGGAAGA
CACGGTCAAAGGCCAGCTCATGTTCACTTTTTCATTAGTGCACCTGGTCA
TAGACACTTAACTACACAGATCAATTTCGCTGGAGATAAATATCTTTGGG
ATGACTTCGCTTACGCAACTAGAGATGGTTTGATTGGTGAATTAAGGTTT
GTTGAGGATGCTGCAGCTGCAAGAGACAGGGGAGTGCAAGGTGAAAGATT
CGCTGAGTTATCATTTGATTTCAGACTTCAGGGTGCAAAGTCTCCAGACG
CTGAAGCAAGATCACATAGACCAAGAGCTTTGCAAGAGGGATGACACCCA
ACTTTTCTATACAAAGTTGTCT
```

attB3-nahG-attB2: Codon-optimized nucleotide sequence encoding NahG from *Pseudomonas* (in red, NCBI Reference Sequence: WP_011475386.1) flanked with Gateway attB3 (5'-end) and attB2 (3'-end) recombination sites (in black):

(SEQ ID NO: 11)

```
ACAACTTTGTATAATAAAGTTGGCATGAAAAATAATAAGTTGGGTTTGAG

AATCGGTATCGTGGGTGGTGGAATATCAGGAGTGGCATTGGCATTGGAAT

TGTGCAGGTATAGTCATATCCAAGTTCAGTTATTTGAGGCTGCACCAGCT

TTCGGAGAAGTTGGTGCAGGAGTGTCCTTTGGTCCTAATGCAGTTAGAGC

TATAGTGGGTTTAGGACTTGGAGAGGCATATCTTCAAGTTGCTGACAGGA

CCTCTGAACCTTGGGAGGATGTGTGGTTCGAATGGAGAAGGGGAAGTGAT

GCTTCCTACTTGGGTGCAACTATTGCTCCAGGAGTTGGACAGTCTTCAGT

GCATAGAGCAGACTTTATCGATGCTTTAGTTACTCACCTTCCTGAAGGAA

TAGCTCAATTCGGTAAAAGAGCAACACAGGTGGAGCAACAGGGTGGAGAA

GTTCAAGTGTTGTTTACTGATGGTACAGAATATAGATGTGACTTGTTAAT

AGGAGCTGATGGTATTAAGAGTGCACTTAGGTCCCATGTTTTGGAAGGAC

AAGGTTTAGCTCCACAGGTGCCTAGATTCTCTGGAACTTGCGCTTATAGG

GGTATGGTTGATTCATTGCATTTGAGAGAGGCATACAGGGCTCATGGTAT

CGACGAACACTTGGTTGATGTGCCACAAATGTACCTTGGATTGGATGGTC

ACATTTTAACATTTCCTGTTAGAAATGGTGGAATTATCAACGTTGTGGCT

TTCATCTCTGACAGGTCAGAACCTAAACCTACCTGGCCAGCTGATGCACC

TTGGGTTAGAGAGGCTTCTCAAAGGGAAATGTTGGACGCTTTTGCAGGAT

GGGGAGATGCTGCTAGAGCTTTGTTGGAATGTATACCAGCACCTACTTTA

TGGGCTCTTCATGACTTGGCAGAATTACCAGGATATGTTCACGGTAGAGT

TGTGTTGATTGGAGATGCTGCACATGCTATGTTACCTCACCAAGGAGCTG

GTGCAGGACAGGGTCTTGAAGATGCATACTTCTTGGCTAGATTACTTGGA

GACACACAAGCTGATGCAGGTAATCTTGCTGAATTGTTGGAGGCTTATGA

TGACTTGAGAAGGCCAAGAGCTTGCAGGGTTCAACAGACCTCATGGGAAA

CTGGAGAGCTTTACGAATTGAGAGATCCTGTTGTGGGAGCTAATGAGCAA

CTTTTGGGTGAAAACTTAGCAACAAGATTTGATTGGCTTTGGAACCATGA

TTTGGACACTGATTTGGCTGAGGCAAGAGCTAGGTTGGGATGGGAACACG

GTGGAGGTGGTGCTTTGAGACAGGGTTGAGACCCAGCTTTCTTGTACAAA

GTGGTCTGA
```

EXAMPLE 1

Production of Muconic Acid in Plants

Muconic acid (MA) is a dicarboxylic acid used for the production of industrially relevant chemicals such as adipic acid, terephthalic acid, and caprolactam. Because the synthesis of these polymer precursors generates toxic intermediates by utilizing petroleum-derived chemicals and corrosive catalysts, the development of alternative strategies for the bio-based production of MA has garnered significant interest. Plants produce organic carbon skeletons by harvesting carbon dioxide and energy from the sun, and therefore represent advantageous hosts for engineered metabolic pathways towards the manufacturing of chemicals. In this work, we engineered *Arabidopsis* to demonstrate that plants can serve as green factories for the bio-manufacturing of MA. In particular, dual expression of plastid-targeted bacterial salicylate hydroxylase (NahG) and catechol 1,2-dioxygenase (CatA) resulted in the conversion of the endogenous salicylic acid (SA) pool into MA via catechol. Sequential increase of SA derived from the shikimate pathway was achieved by expressing plastid-targeted versions of bacterial salicylate synthase (Irp9) and feedback-resistant 3-deoxy-D-arabino-heptulosonate synthase (AroG). Introducing this SA over-producing strategy into engineered plants that co-express NahG and CatA resulted in a 50-fold increase in MA titers. Considering that MA is easily recovered from senesced plant biomass after harvest, the phytoproduction of MA is envisioned as a beneficial option to add value to bioenergy crops.

Figure 2A:
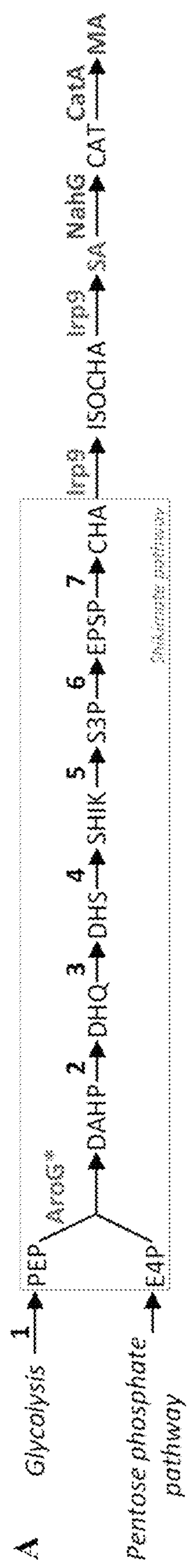
FIG. 2A. Strategy used for the production of muconic acid in plants. De novo biosynthetic pathway for muconic acid synthesis. Bacterial enzymes AroG*, Irp9, NahG, and CatA are expressed in *Arabidopsis* for the production of muconic acid from salicylic acid derived from the shikimate pathway. Abbreviations are: CAT, catechol; CHA, chorismate; DAHP, 3-deoxy-D-arabino-heptulosonate; DHQ, dehydroquinate; DHS, dehydroshikimate; E4P, erythrose 4-phosphate; EPSP, 5-enolpyruvoylshikimate 3-phosphate; F6P, fructose 6-phosphate; G3P, glyceraldehyde 3-phosphate; ISOCHA, isochorismate; MA, muconic acid; PEP, phosphoenolpyruvate; PYR, pyruvate; S3P, shikimate 3-phosphate; SA, salicylic acid; SHIK, shikimate. The enzymes are as follows: 1, enolase; AroG*, feedback-resistant DAHP synthase (L175Q); 2, DHQ synthase; 3, DHQ dehydratase; 4, shikimate dehydrogenase; 5, shikimate kinase; 6, EPSP synthase; 7, chorismate synthase; Irp9, bifunctional ISOCHA synthase/ISOCHA pyruvate lyase; NahG, salicylate hydroxylase; CatA, catechol 1,2-dioxygenase.

In plants, the shikimate pathway is confined to plastids and provides the precursors for the synthesis of aromatic amino acids and derived metabolites, vitamins $K_1$ and $B_9$, and SA (Maeda and Dudareva, 2012). *Arabidopsis* is used as a model system to investigate a novel bio-based approach for the phytoproduction of MA. In particular, the SA pool derived from chorismate via the shikimate pathway is converted to catechol and MA by dual expression and plastid-targeting of bacterial salicylate hydroxylase (NahG) and catechol 1,2-dioxygenase (CatA) (FIG. 2A). Additional supply of SA to the MA pathway is achieved via the expression of bacterial salicylate synthase Irp9 and feedback-resistant 3-deoxy-D-arabino-heptulosonate (DAHP) synthase (AroG*), which results in a ~50-fold increase of MA content. Importantly, MA is recovered from the biomass of senesced mature plants which highlights its stability and suitability for storage when produced in target crops. Therefore, such engineered crops could represent high-potential feedstocks for existing MA microbial production platforms towards sustainable development of bio-based MA.

2. Material and Methods

2.1. Plant Material and Growth Conditions

*Arabidopsis thaliana* (ecotype Columbia, Col-0) seeds are germinated directly on soil. Growing conditions are 150 μmol/m²/s, 22° C., 60% humidity and 10 h of light per 24-h day cycle. Selection of T2 and identification of T3 homozygous transgenic plants is made on Murashige and Skoog vitamin medium (PhytoTechnology Laboratories, Shawnee Mission, Kans.), supplemented with 1% sucrose, 1.5% agar, 50 μg/mL kanamycin and/or 25 μg/mL hygromycin.

2.2. Construction of Plasmids and Plant Transformation

To generate the pA6-pIRX5::schl1-irp9 construct, a gene sequence encoding Irp9 from *Yersinia enterocolitica* (GenBank accession number CAB46570.1) containing the encoding sequence of the plastid transit peptide (schl1) from the *Arabidopsis* ferredoxin2 (At1g60950) (Xue et al., 2013), and flanked with the Gateway attB1 (5'-end) and attB2 (3'-end) recombination sites is synthesized for expression in *Arabidopsis* (attB1-schl1-irp9-attB2, Supplementary Data S1) (GenScript, Piscataway, N.J.). This sequence is cloned into the Gateway pDONR221-P1P2 entry vector by BP recombination (Life Technologies, Foster City, Calif.). An entry clone is LR recombined with the pA6-pIRX5::GWR1R2 vector (Vega-Sanchez et al., 2015) to generate the pA6-pIRX5::schl1-irp9 construct.

To generate the pA6-pIRX5::schl1-irp9-pCCoAOMT::schl2-aroG construct (FIG. 2B), the attB1-schl1-irp9-attB2 sequence is amplified by PCR to replace the Gateway attB2 recombination site (3'-end) by an attB4 recombination site, and cloned into the Gateway pDONR221-P1P4 entry vector by BP recombination (Life Technologies, Foster City, Calif.) to produce a pDONR221-L1-schl1-irp9-L4 construct. A chimeric DNA construct is synthesized (GenScript, Piscataway, N.J.): it is flanked by the gateway sequences attB4r (5'-end) and attB3r (3'-end), and contains the tG7 terminator and a 2.2-Kb sequence corresponding to the *Arabidopsis* CCoAOMT1 (At4g34050) promoter (pCCoAOMT). This attB4r-tG7-pCCoAOMT-attB3r construct (Supplementary Data S1) is then subcloned into the Gateway pDONR221-P4rP3r entry vector by BP recombination (Life Technologies, Foster City, Calif.) to produce pDONR221-L4R-tG7-pCCoAOMT-L3R. A gene sequence encoding feedback-insensitive AroG (L175Q) from *E. coli* (NCBI Reference Sequence: WP_032246946.1) containing the encoding sequence of the transit peptide (schl2) of the pea (*Pisum sativum*) ribulose-1,5-bisphosphate carboxylase small subunit (GenBank: AAG45569.1) (Tzin et al., 2012), and flanked with the Gateway attB3 (5'-end) and attB2 (3'-end) recombination sites is synthesized for expression in *Arabidopsis* (attB3-schn-aroG-attB2, Supplementary Data S1) (GenScript, Piscatway, N.J.). This sequence is cloned into the Gateway pDONR221-P3P2 entry vector by BP recombination (Life Technologies, Foster City, Calif.) to produce the pDONR221-P3-schn-aroG-P2 construct. A multi-site LR recombination (Life technologies, Foster City, Calif., USA) using the pDONR221-L1-schl1-irp9-L4, pDONR221-L4R-tG7-pCCoAOMT-L3R, and pDONR221-L3-schn-aroG-L2 entry vectors and the pA6-pIRX5::GWR1R2 destination vector is performed to generate the pA6-p1RX5::schl1-irp9-pCCoAOMT::schl2-aroG construct.

To generate the pTkan-pIRX8-schl3-catA-pC4H-schl3-nahG construct (FIG. 2B), a gene sequence encoding CatA from *Pseudomonas putida* (NCBI Reference Sequence: WP_010954549.1) containing the encoding sequence of the transit peptide (schl3) of the sunflower (*Helianthus annuus*) ribulose-1,5-bisphosphate carboxylase small subunit (UniProtKB/Swiss-Prot: P08705.1) (Lebrun et al., 1992, Eudes et al., 2015), and flanked with the Gateway attB1 (5'-end) and attB4 (3'-end) recombination sites is synthesized for expression in *Arabidopsis* (attB1-schl3-catA-attB4, Supplementary Data 51) (GenScript, Piscatway, N.J.). This sequence is cloned into the Gateway pDONR221-P1P4 entry vector by BP recombination (Life Technologies, Foster City, Calif.) to produce the pDONR221-L1-schl3-catA-L4 construct. A gene sequence encoding NahG from *Pseudomonas putida* (NCBI Reference Sequence: WP_011475386.1) and flanked with the Gateway attB3 (5'-end) and attB2 (3'-end) recombination sites is synthesized for expression in *Arabidopsis* (attB3-nahG-attB2, Supplementary Data 51) (GenScript, Piscatway, N.J.). This sequence is cloned into the Gateway pDONR221-P3P2 entry vector by BP recombination (Life Technologies, Foster City, Calif.) to produce the pDONR221-L3-nahG-L2 construct. A multi-site LR recombination (Life Technologies, Foster City, Calif.) using the pDONR221-L1-schl3-catA-L4, pDONR221-L4R-tg7-pC4H::schl3-L3R (Eudes et al., 2015), and pDONR221-L3-nahG-L2 entry vectors and the pTKan-pIRX8::GWR1R2 (Yang et al., 2013) destination vector is performed to generate the pTkan-pIRX8-schl3-catA-pC4H-schl3-nahG construct. The constructs are introduced into wild-type *Arabidopsis* plants (ecotype Col0) via *Agrobacterium tumefaciens*-mediated transformation (Bechtold and Pelletier, 1998).

2.3. RNA Extraction and qRT-PCR Analysis

Total RNA is extracted from stems of 5-week-old wild type and T3 homozygous transgenic lines (pools of three plants per line, ~100 mg) using the Plant RNeasy extraction kit (Qiagen, Valencia, Calif.), and treated with DNase (Qiagen, Valencia, Calif.) to remove genomic DNA contamination. First-strand cDNAs are synthesized from 2 μg of total RNA using the SuperScript III First-Strand Synthesis SuperMix (Thermo Fisher Scientific, Waltham, Mass.) followed by qPCR analysis using SsoAdvanced Universal SYBR Green Supermix (Bio-Rad, Hercules, Calif.) on a CFX96 Real-Time PCR Detection System (Bio-Rad, Hercules, Calif.) following the manufacturer's instruction. Oligonucleotide primers (Table 1) are tested in annealing temperature gradients and 58° C. was chosen as the annealing temperature. Melting curve analyses are performed after each run to ensure single amplicons are produced. The data are analyzed using the $2^{(-\Delta\Delta Ct)}$ method (Livak and Schmittgen, 2011).

TABLE 1

Oligonucleotides used in Example 1.

| Primer name | Sequence (5'-3') |
|---|---|
| Irp9-F | TGTAGAAGGTTGTGCGAGTG (SEQ ID NO: 12) |
| Irp9-R | CTTCACGTATTCTCCCCTTCTG (SEQ ID NO: 13) |
| CatA-F | TTGGGATGACTTCGCTTACG (SEQ ID NO: 14) |
| CatA-R | GGAGACTTTGCACCCTGAAG (SEQ ID NO: 15) |
| nahG-F | CAAAGGGAAATGTTGGACGC (SEQ ID NO: 16) |
| nahG-R | GCATCTCCAATCAACACAACTC (SEQ ID NO: 17) |
| aroG-F | GATGTTTGTGCTGACGTGTG (SEQ ID NO: 18) |
| aroG-R | TTCCCTCAACTAAGTGACTTTCC (SEQ ID NO: 19) |
| ACT2-F | GGTAACATTGTGCTCAGTGGTGG (SEQ ID NO: 20) |
| ACT2-R | AACGACCTTAATCTTCATGCTGC (SEQ ID NO: 21) |

2.4. Metabolite Extraction

SA is extracted from developing stems using 80% (v/v) methanol-water at 70° C. as previously described (Eudes et al., 2015). MA is extracted from stems of mature senesced plants ball-milled with a mixer mill MM 400 (Retsch, Newtown, Pa.). Ball-milled stem material (50 mg) is mixed with 1 mL of 80% (v/v) methanol-water and mixed (1400 rpm) for 15 min at 70° C. This extraction step is repeated twice. Extracts are pooled and cleared by centrifugation (5 min, 20,000×g), mixed with 1.5 mL of analytical grade water and filtered using Amicon Ultra centrifugal filters (3000 Da MW cutoff regenerated cellulose membrane; EMD Millipore, Billerica, Mass.) prior to LC-MS analysis.

Alternatively, MA is released from stems of mature senesced plants (line nahG-catA-1.2×irp9-aroG 2.2) using dilute alkaline and dilute acid treatments. For dilute alkaline treatments, 10 mg of ball-milled biomass is soaked with 90 μL of either 1.2% or 0.62% (w/v) NaOH and heated at 100° C. or 130° C. for 30 min in an autoclave, respectively. For dilute acid treatment, biomass (10 mg) is soaked with 90 μL of 1.2% (w/v) $H_2SO_4$ and heated at 120° C. for 30 min in an autoclave. After cooling down and centrifugation, an aliquot of the hydrolysates is mixed with 4 volumes of 80% (v/v) methanol-water and filtered using Amicon Ultra centrifugal filters prior to LC-MS analysis.

2.5. LC-MS Metabolite Analysis

SA and catechol are analyzed using liquid chromatography (LC), electrospray ionization (ESI), and time-of-flight (TOF) mass spectrometry (MS) as previously described (Haushalter et al., 2017). LC-ESI-TOF-MS analysis of muconic acid is carried out with a similar method except that the LC gradient elution is conducted as follows: linearly increased from 5% solvent B (0.1% formic acid in methanol)

to 60.9% B in 4.3 min, increased from 60.9% B to 97.1% B in 1.3 min, decreased from 97.1% B to 5% B in 0.4 min, and held at 5% B for 2 min. The flow rate is held at 0.42 mL/min for 5.6 min, increased from 0.42 mL/min to 0.65 mL/min in 0.4 min, and held at 0.65 mL/min for 2 min. The total LC run time is 8 min. All metabolites are quantified via calibration curves of standard compounds (Sigma-Aldrich, St Louis, Mo.) for which the $R^2$ coefficients were ≥0.99. Cis,trans-MA is prepared from cis,cis-MA as previously described (Matthiesen et al., 2016).

3. Results 3.1. Muconic Acid (MA) Production in Plants Expressing nahG and catA

Figure 6A:
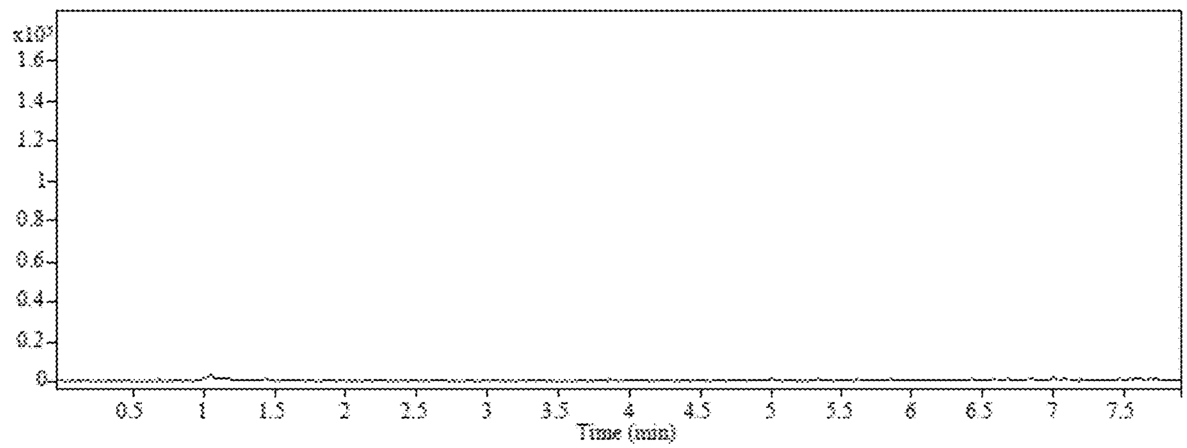
FIG. 6A. Representative LC-TOF MS chromatogram of muconic acid extracted from *Arabidopsis* biomass. A sample from wild-type control plants.
Figure 6B:
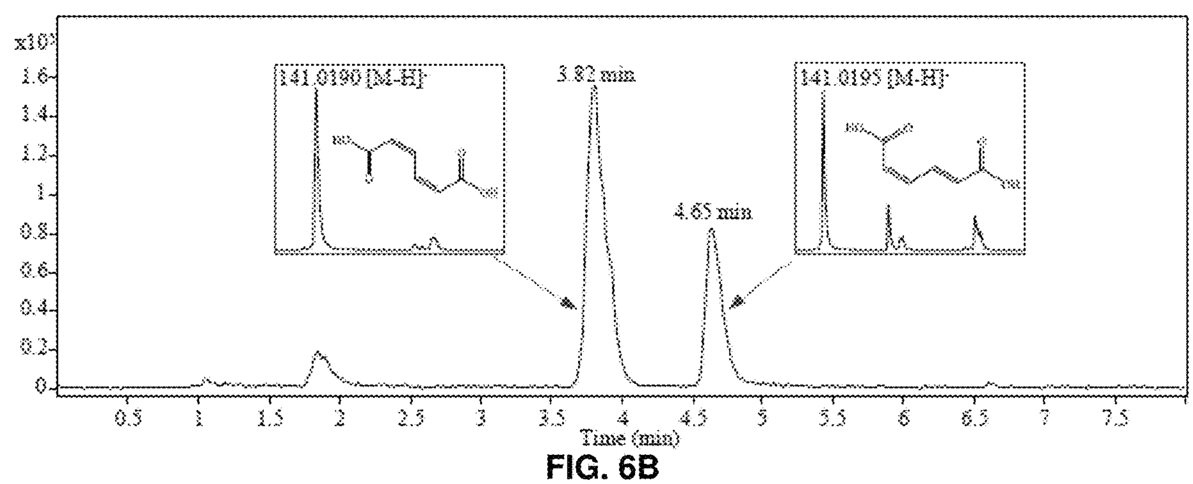
FIG. 6B. Representative LC-TOF MS chromatogram of muconic acid extracted from *Arabidopsis* biomass. A sample from nahG-catA transgenic plants.
Figure 6C:
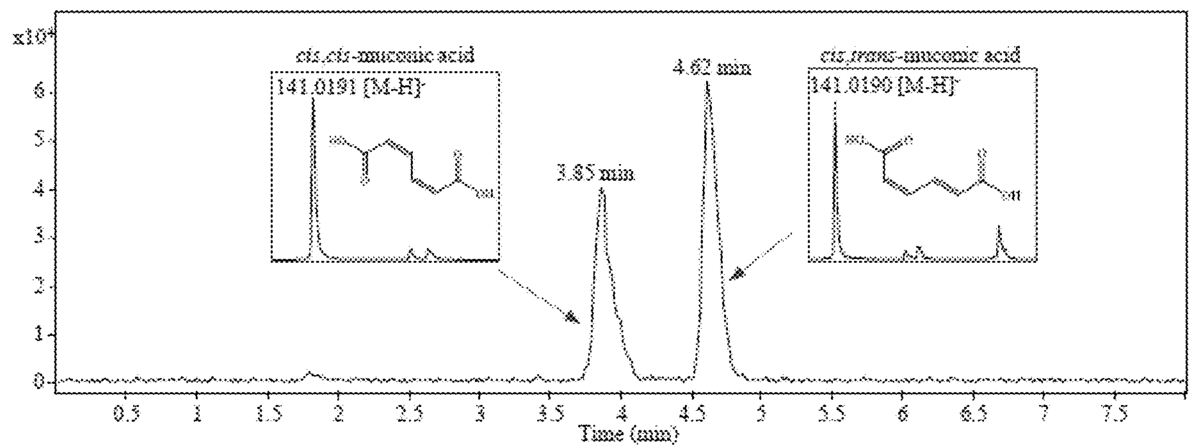
FIG. 6C. Representative LC-TOF MS chromatogram of muconic acid extracted from *Arabidopsis* biomass. cis,cis- and cis,trans-muconic acid standards.

The plastidial SA pool derived from the shikimate pathway is used as precursor for the biosynthesis of MA in *Arabidopsis* stems. To this end, plastid-targeted versions of the salicylate hydroxylase NahG and catechol 1,2-dioxygenase CatA from *Pseudomonas putida* are co-expressed for the sequential conversion of SA into catechol and MA. Although NahG has been shown previously to be functional in plants (Friedrich et al., 1995), the use of CatA for the synthesis of MA in plants has never been described. Since mature senesced *Arabidopsis* plants mainly consist of stem biomass, two *Arabidopsis* promoters (pIRX8 and pC4H) which are both strongly active in stem tissues that develop secondary cell walls for synchronized expression of nahG and catA (FIG. 2B) are selected. Specifically, both promoters are known to be active in xylem vessels and interfascicular fibers: pIRX8 is the promoter of a glycosyltransferase family 8 (GT8) involved in the synthesis of secondary cell wall xylan (Persson et al., 2007), and pC4H is the promoter of the cytochrome P450 cinnamate 4-hydroxylase involved in the general phenylpropanoid pathway and lignin biosynthesis (Bell-Lelong et al., 1997). Five independent lines are selected, and expression of nahG and catA was confirmed by RT-qPCR using mRNA extracted from stems of 5-week-old homozygous plants at the T3 generation (FIG. 3A). For these five lines, the content of MA extracted from stem biomass of senesced plants vary between 8.3 and 13.8 μg/g DW (FIG. 3B), which validates the dual nahG-catA expression strategy for the production of MA in plants. Although CatA converts catechol into cis,cis-MA, a mixture of cis,cis-MA and cis, trans-MA in the plant extracts are detected (FIGS. 6A to 6C), presumably due to the partial conversion of cis,cis-MA acid during the extraction procedure performed at 70° C. Therefore, MA titers reported in this Example 1 are the sum of cis,cis-MA acid and cis,trans-MA. Moreover, SA content measured in 5-week-old stems from the transgenic lines that co-express nahGand catA is reduced 5- to 10-fold compared to wild-type plants (FIG. 3C), suggesting that SA can be limiting for MA synthesis in transgenics.

3.2. Enhancement of SA Content in Stems by Expressing Bacterial Salicylate Synthase (Irp9) and Feedback-Insensitive DAHP Synthase (AroG*)

Figure 4A:
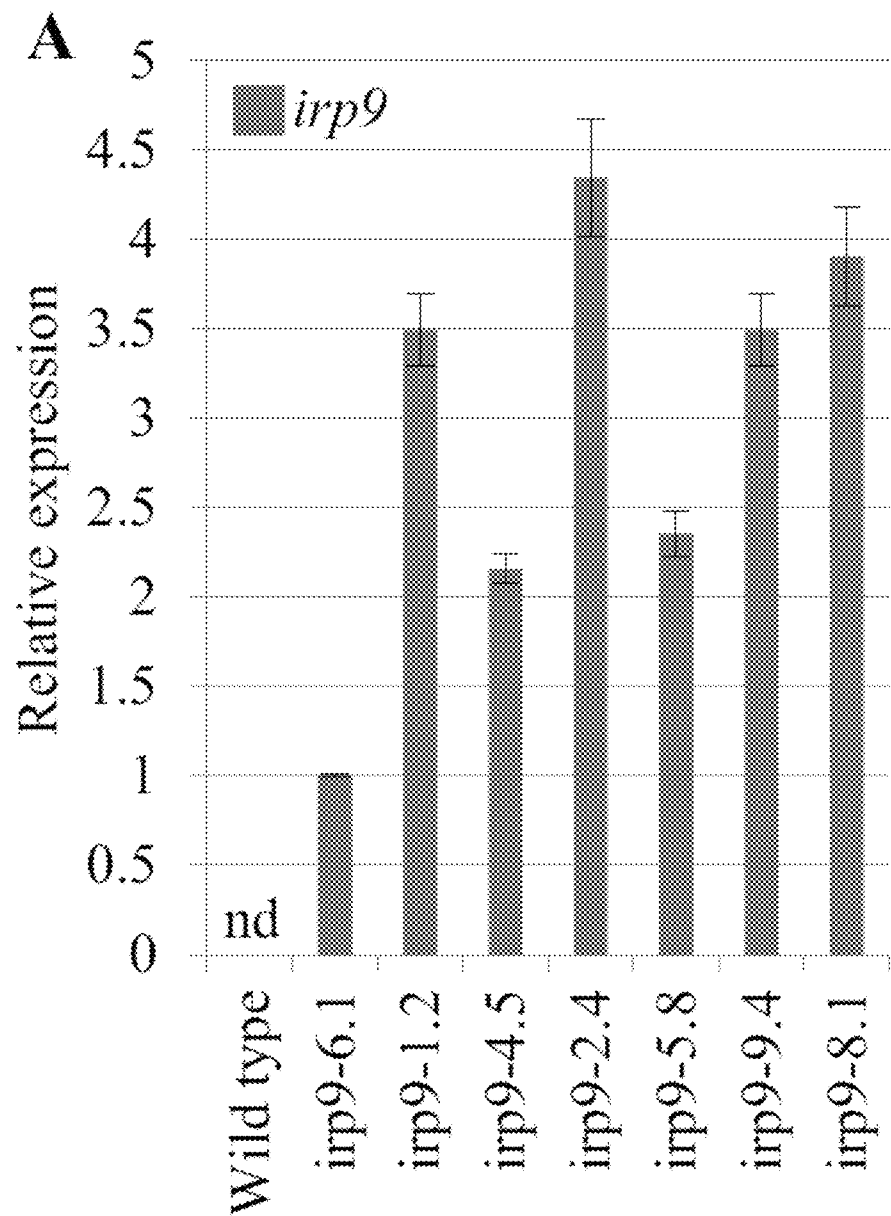
FIG. 4A. Overproduction of SA in plants expressing Irp9 and feedback-resistant DAHP synthase (AroG*). Detection by qRT-PCR of mRNA expression levels in stems from 5-week-old wild type and pA6-pIRX5::schl1-irp9 (irp9) transgenic lines. ACT2is used as an internal control. Irp9 expression level is normalized to 1 in line irp9-6.1 and is calculated relative to this value in the other lines. Error bars represent the SD from technical duplicates.
Figure 4B:
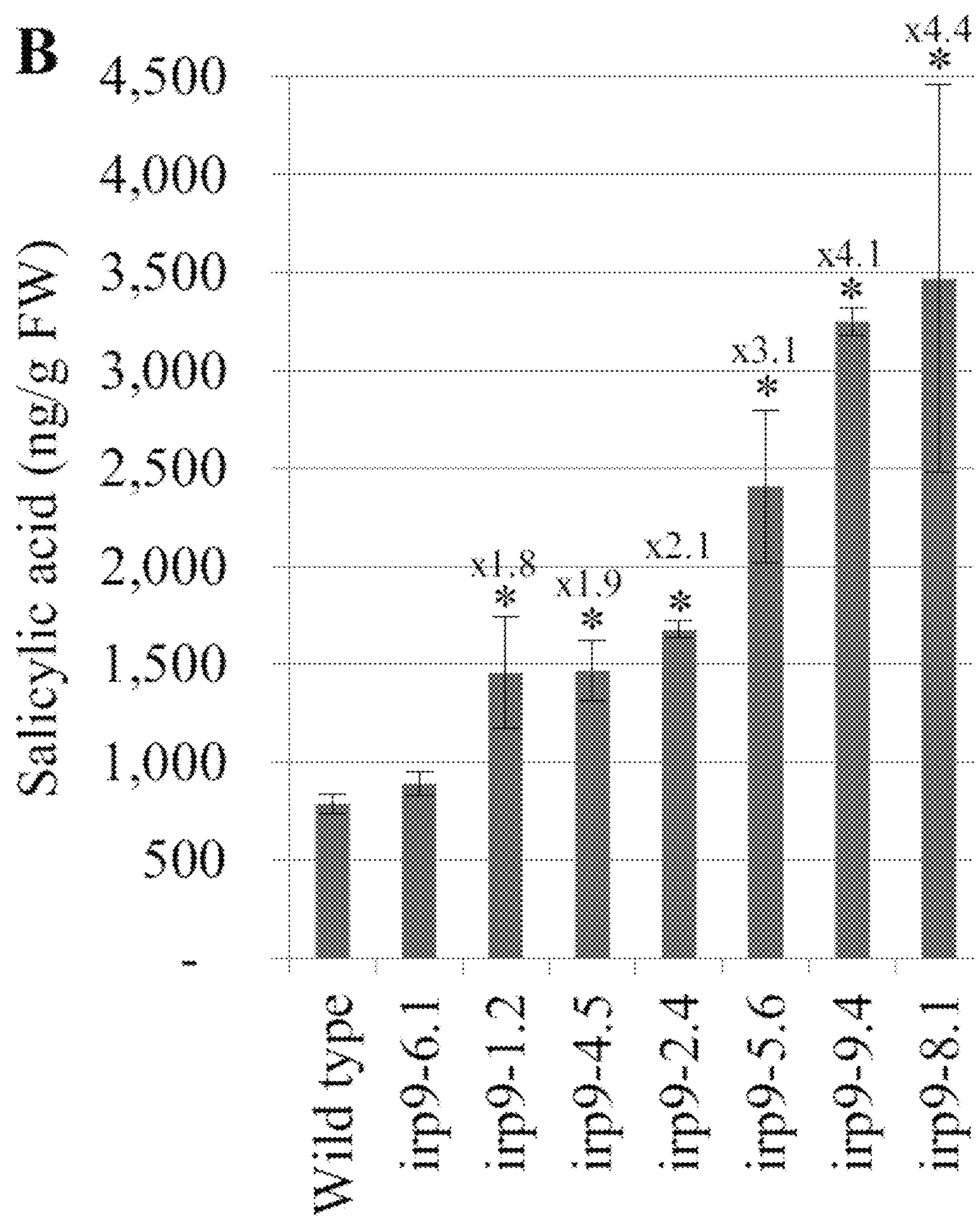
FIG. 4B. Overproduction of SA in plants expressing Irp9 and feedback-resistant DAHP synthase (AroG*). SA content in stems of 5-week-old wild type and irp9 transgenic lines. Error bars represent the SE from four biological replicates (n=4). Asterisks indicate significant differences from the wild type using the unpaired Student's t-test (*P<0.005).
Figure 4C:
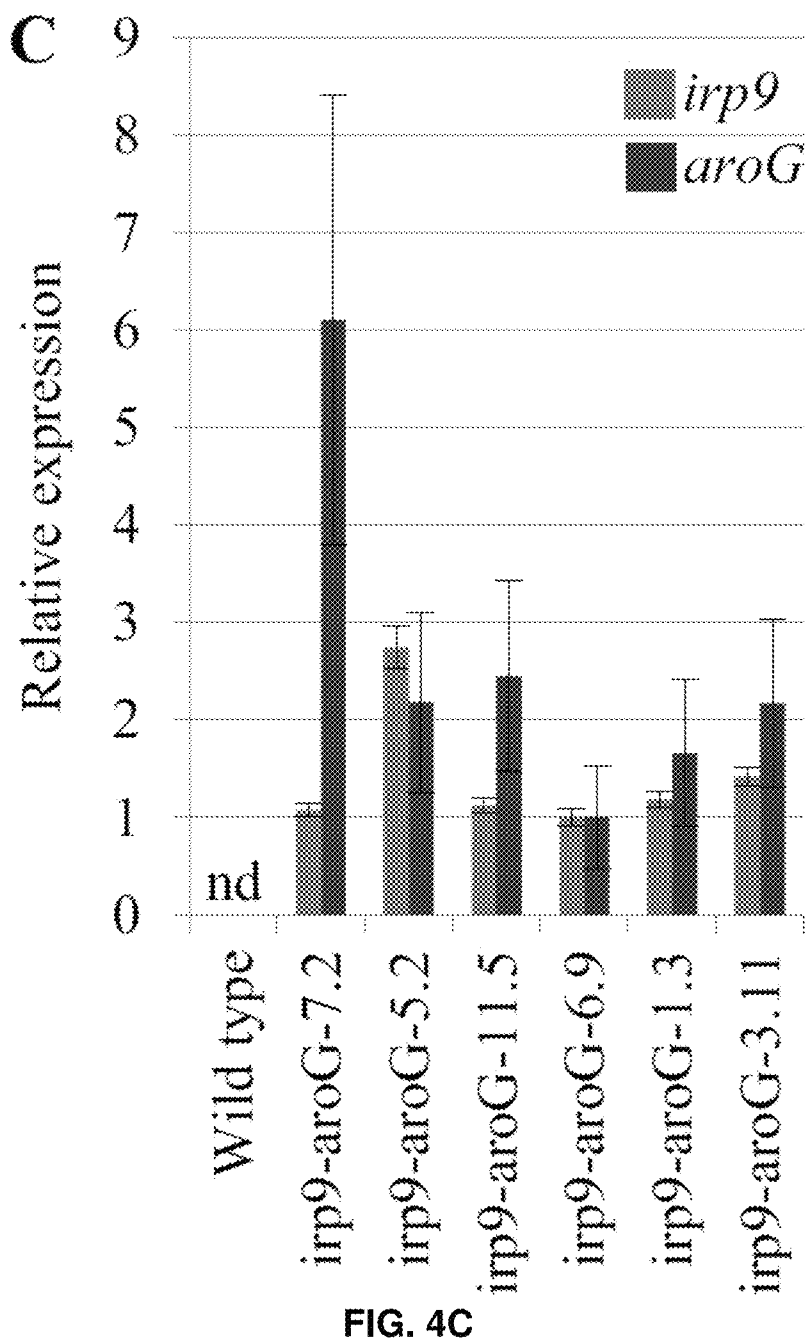
FIG. 4C. Overproduction of SA in plants expressing Irp9 and feedback-resistant DAHP synthase (AroG*). Detection by qRT-PCR of mRNA expression levels in 15-cm stems from wild type and pA6-pIRX5::schl1-irp9-pCCoAOMT::schl2-aroG(irp9-aroG) transgenic lines. ACT2 is used as an internal control. Irp9 and aroG expression levels are normalized to 1 in line irp9-aroG-6.9 and are calculated relative to these values in the other lines. Error bars represent the SD from technical duplicates.
Figure 4D:
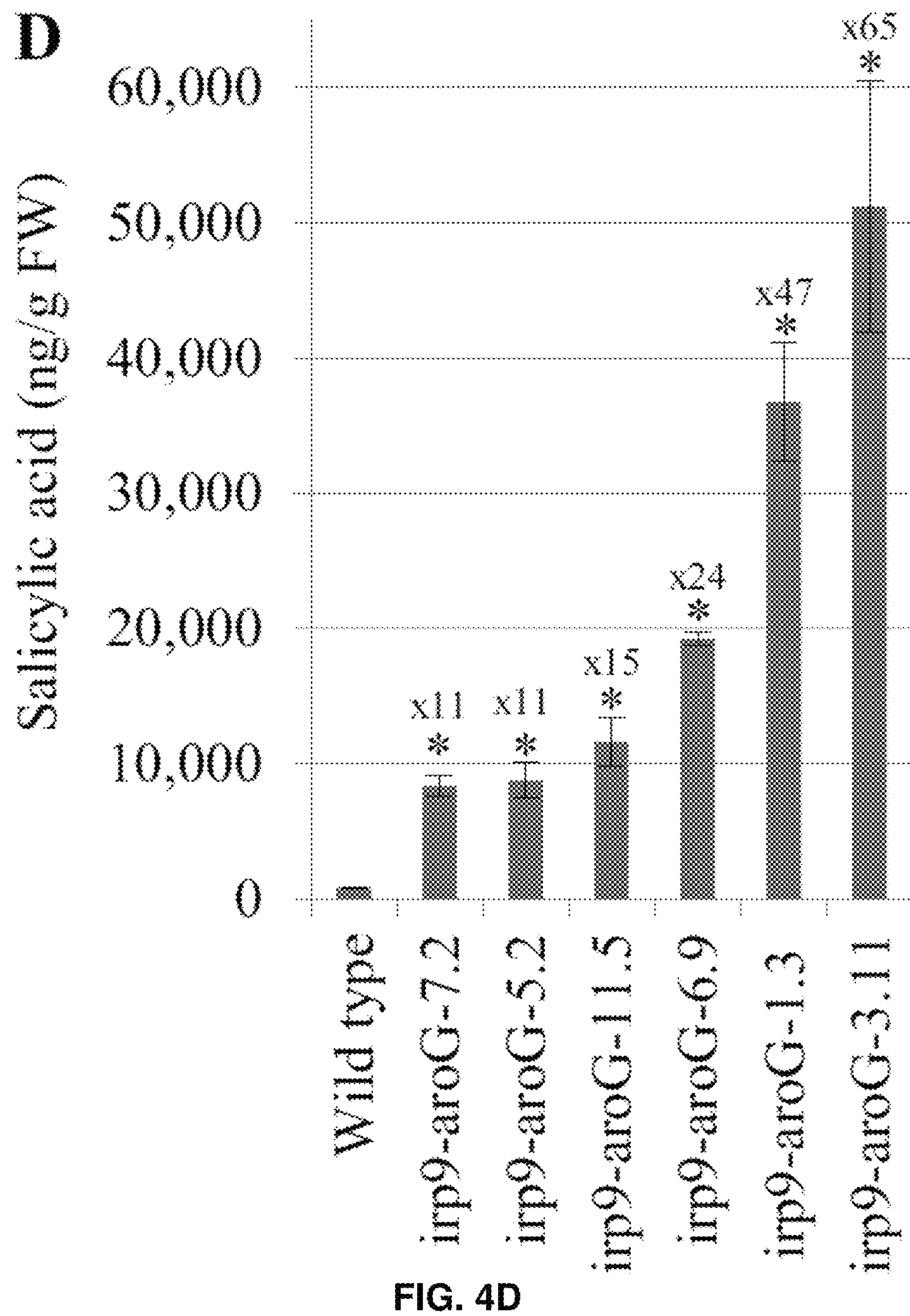
FIG. 4D. Overproduction of SA in plants expressing Irp9 and feedback-resistant DAHP synthase (AroG*). SA content in 15-cm stems of wild type and irp9-aroG transgenic lines. Error bars represent the SE from four biological replicates (n=4). Asterisks indicate significant differences from the wild type using the unpaired Student's t-test (*P<0.001).

In order to increase the content of SA in *Arabidopsis* stems, a plastid-targeted version of the salicylate synthase Irp9 from *Yersinia enterocolitica* is expressed using the promoter of the *Arabidopsis* secondary cell wall cellulose synthase gene IRX5 (CESA4) which is specifically active in stem vascular tissues (Eudes et al., 2012). Expression of irp9 has previously been shown to be effective to increase SA content without negative growth consequences in poplar (Xue et al., 2013). Seven independent lines are selected and expression of irp9 is confirmed by RT-qPCR using mRNA extracted from stems of 5-week-old homozygous plants at the T3 generation (FIG. 4A). For six of these seven lines, the content of SA extracted from 5-week-old stems is increased significantly 1.8- to 4.4-fold compared to wild-type plants (FIG. 4B), which validates the important role of Irp9 to increase SA content in *Arabidopsis* stems. None of these transgenic lines show any visible growth defects. Next, in order to further increase the carbon flux through the SA biosynthesis pathway in stem, a new set of transgenic lines is generated for co-expression of Irp9 with a mutant feedback-insensitive DAHP synthase (AroG*) from *E. coli.* Expression of plastid-targeted AroG* in *Arabidopsis* is previously shown to increase the content of metabolites derived from the shikimate pathway such as aromatic amino acids and hydroxycinnamates (Tzin et al., 2012). The promoter pCCoAOMT of the caffeoyl-CoA O-methyltransferase gene involved in the monolignol pathway and lignin biosynthesis in *Arabidopsis* is chosen to express aroG* in stem vascular tissues that produce secondary cell walls (Do et al., 2007). Expression of irp9 and aroG* is verified in six independent lines using mRNA extracted from 15-cm stems of homozygous plants at the T3 generation (FIG. 4C). For these six lines, the content of SA extracted from 15-cm stems is increased significantly 11- to 65-fold compared to wild-type plants (FIG. 4D). The two lines showing the highest SA increase (irp9-aroG-1.3 and irp9-aroG-3.11) have an obvious dwarf phenotype compared to the other lines and wild-type plants, a phenomenon previously observed in *Arabidopsis* mutants that overproduce SA (Sha, 2003). Therefore, co-expression of Irp9 and AroG* genes under secondary cell wall promoters represents an efficient strategy for over-producing SA in *Arabidopsis* stems.

3.3. MA Production in Plants Expressing NahG, CatA, Irp9, and AroG*

Figure 2B:
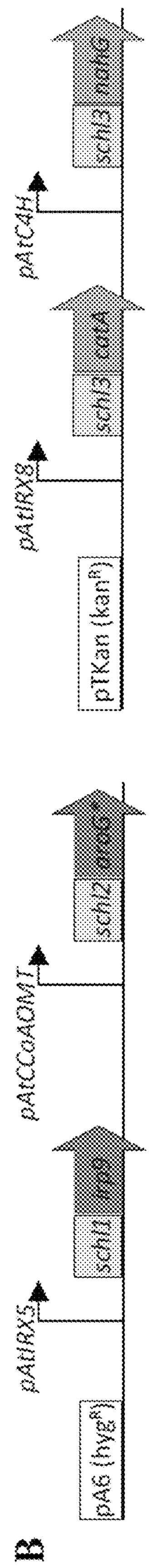
FIG. 2B. Strategy used for the production of muconic acid in plants. Binary vectors used in Example 1. Boxes labelled "schl" denote plastid transit peptides. pA6 and pTKan denote the two binary vector backbones conferring hygromycin (hyg$^R$) and kanamycin (kan$^R$) resistance in plants. Abbreviations are: schl1, plastid transit peptide from *Arabidopsis* ferredoxin2 (At1g60950); schl2, plastid transit peptide from pea (*Pisum sativum*) ribulose-1,5-bisphosphate carboxylase small subunit (GenBank: AAG45569.1); schl3, plastid transit peptide sunflower (*Helianthus annuus*) ribulose-1,5-bisphosphate carboxylase small subunit (UniProtKB/Swiss-Prot: P08705.1). pAtIRX5, pAtCCoAOMT, pAtIRX8, and pAtC4H designate the promoters of *Arabidopsis* cellulose synthase 4 (At5G44030), caffeoyl coenzyme A O-methyltransferase 1 (At4G34050), galacturonosyltransferase 12 (At5G54690), and cinnamate 4-hydroxylase (At2G30490) genes, respectively.
Figure 3A:
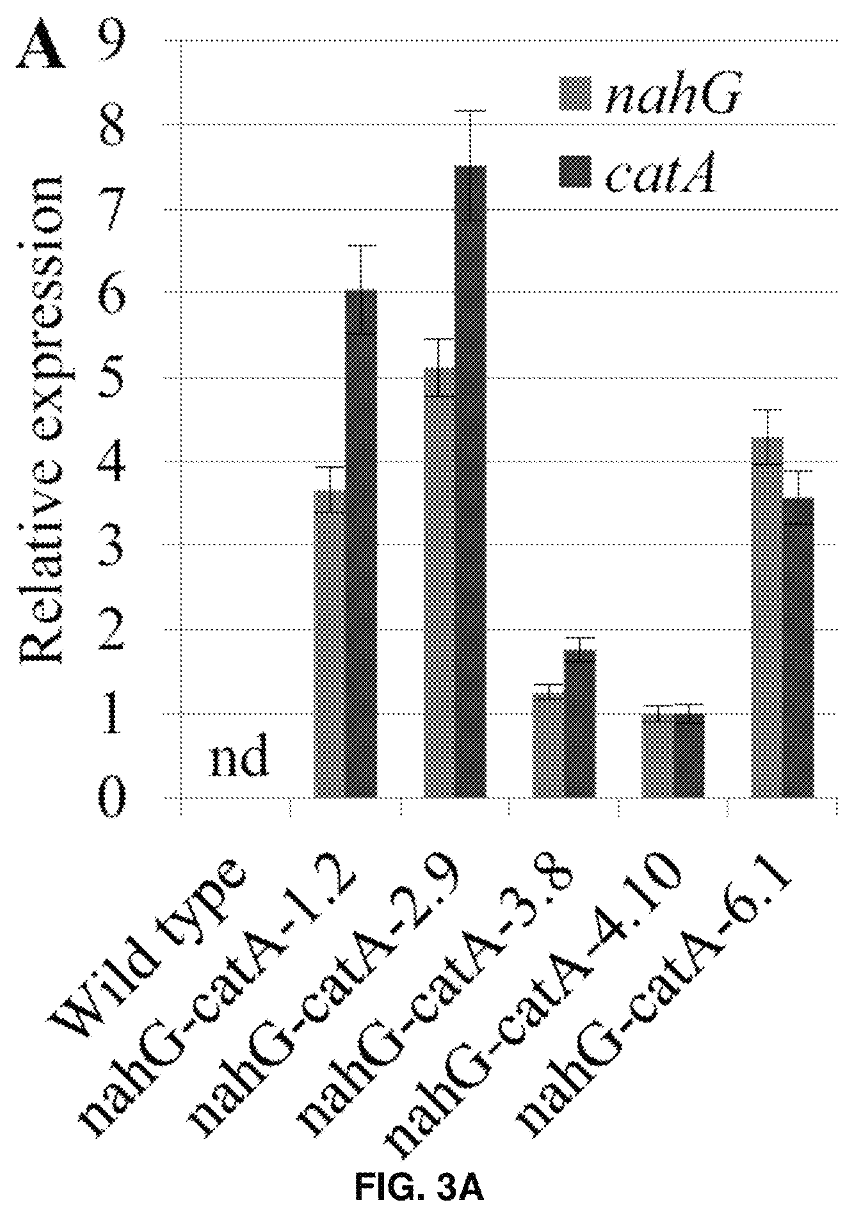
FIG. 3A. MA and SA production in plants expressing bacterial NahG and CatA. Detection by qRT-PCR of mRNA expression levels in stems from 5-week-old wild type and pTkan-pIRX8-schl3-catA-pC4H-schl3-nahG (nahG-catA) transgenic lines. ACT2is used as an internal control. Expression levels of nahG and catA are normalized to 1 in line nahG-catA-4.10 and are calculated relative to these values in the other lines. Error bars represent the SD from technical duplicates. Error bars represent the SE from four biological replicates (n=4). Asterisks indicate significant differences from the wild type using the unpaired Student's t-test (*P<0.005).
Figure 3B:
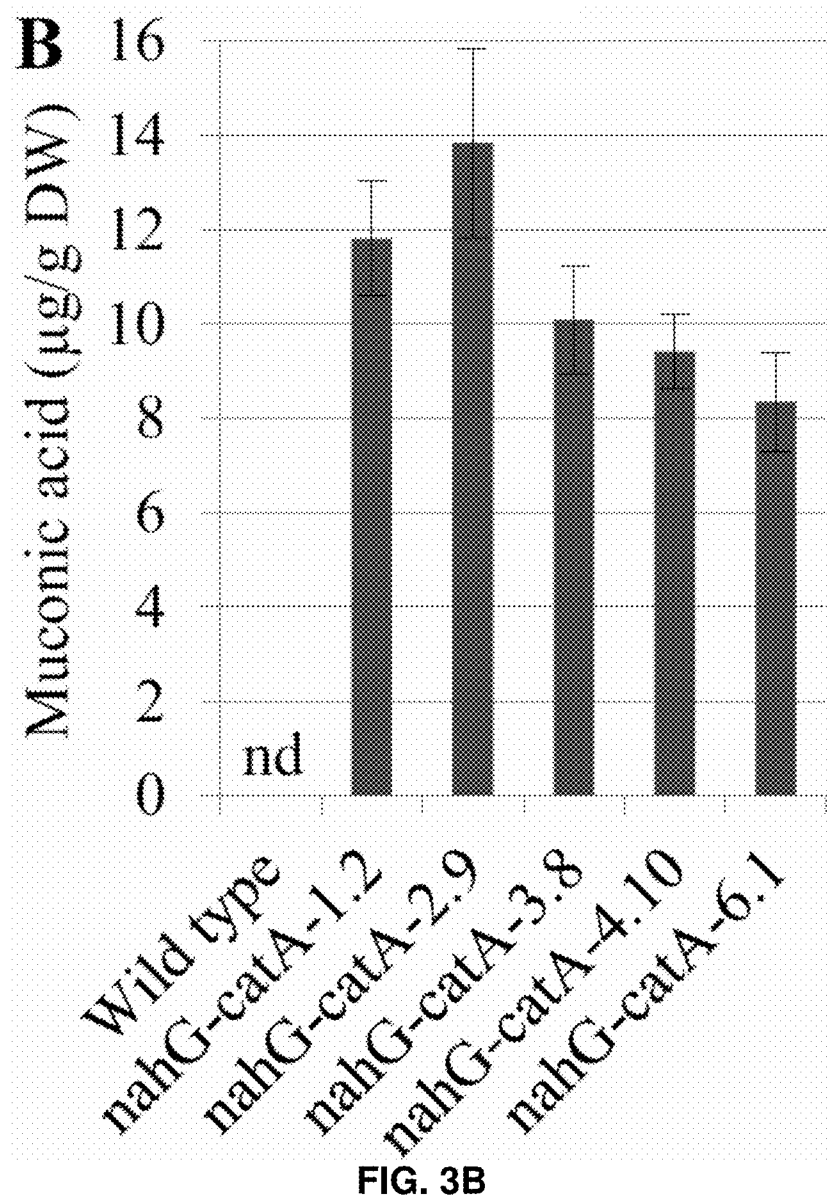
FIG. 3B. MA and SA production in plants expressing bacterial NahG and CatA. MA content in mature senesced dried stems of wild type and nahG-catA transgenic lines. Error bars represent the SE from four biological replicates (n=4). (C) SA content in stems of 5-week-old wild type and nahG-catA transgenic lines. Error bars represent the SE from four biological replicates (n=4). Asterisks indicate significant differences from the wild type using the unpaired Student's t-test (*P<0.005).
Figure 3C:
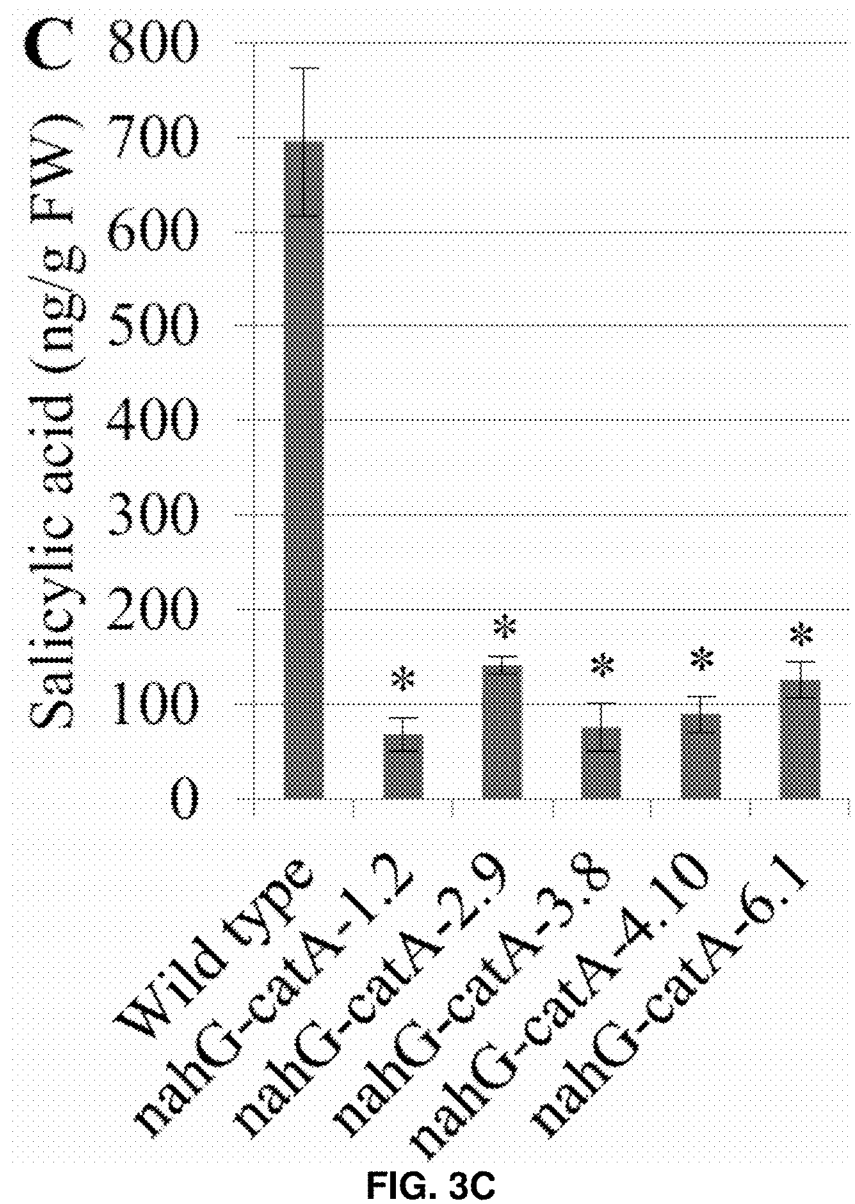
FIG. 3C. MA and SA production in plants expressing bacterial NahG and CatA. SA content in stems of 5-week-old wild type and nahG-catA transgenic lines. Error bars represent the SE from four biological replicates (n=4). Asterisks indicate significant differences from the wild type using the unpaired Student's t-test (*P<0.005).
Figure 5A:
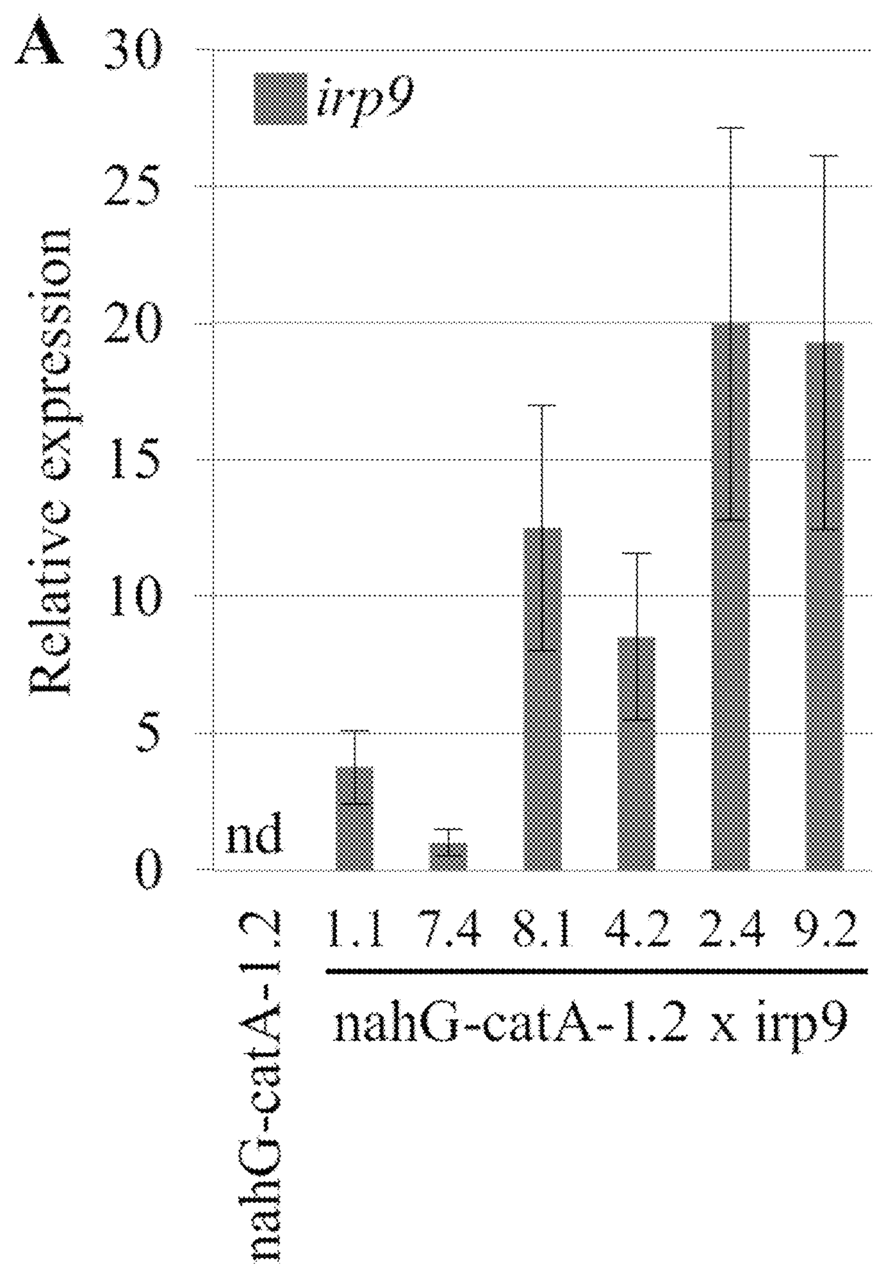
FIG. 5A. MA production in plants expressing bacterial NahG, CatA, Irp9 and AroG*. Detection by qRT-PCR of mRNA expression levels in stems from 5-week-old nahG-catA-1.2 and nahG-catA-1.2×irp9 transgenic lines. ACT2 is used as an internal control. Irp9 expression level is normalized to 1 in line nahG-catA-1.2×irp9 7.4 and is calculated relative to this value in the other lines. Error bars represent the SD from technical duplicates.
Figure 5B:
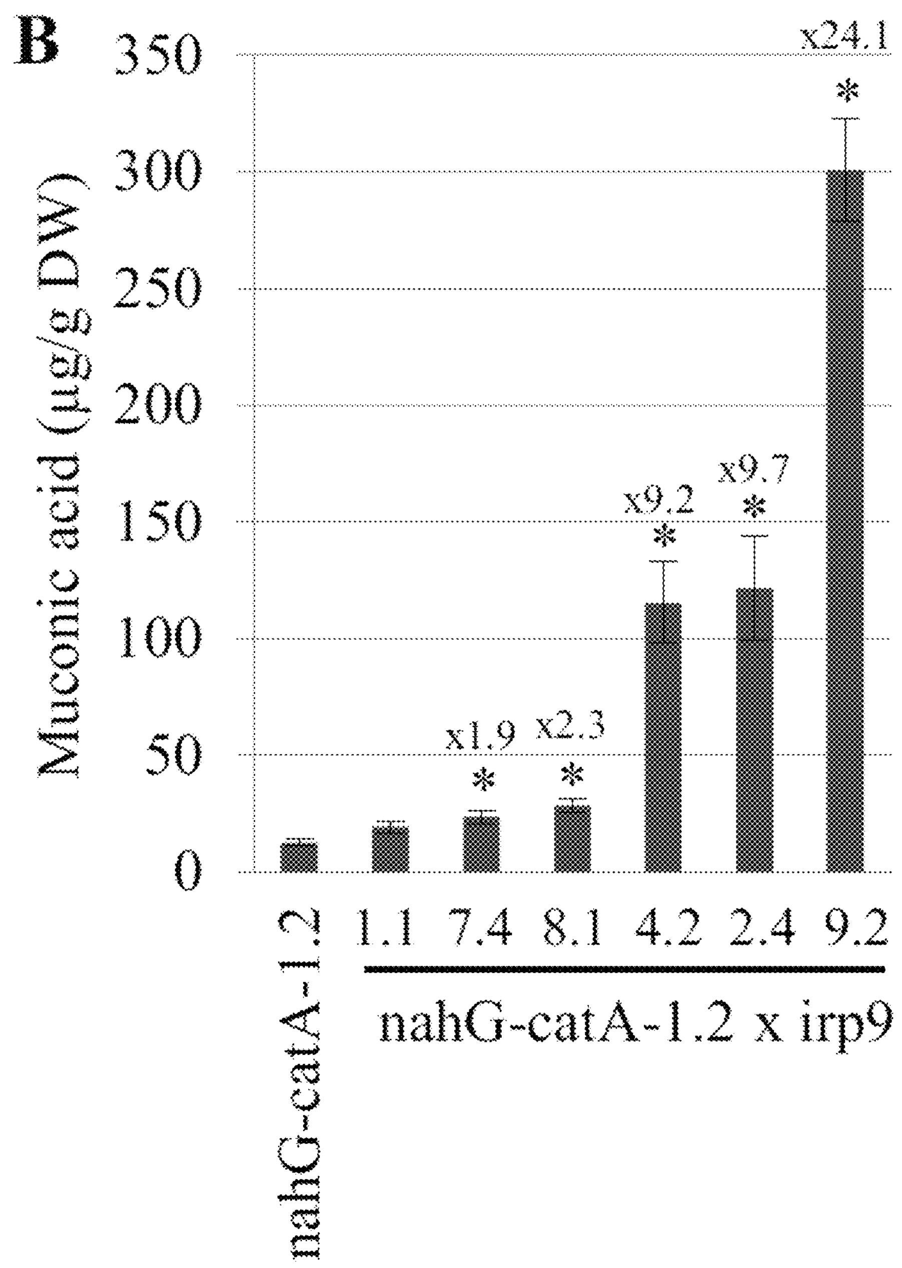
FIG. 5B. MA production in plants expressing bacterial NahG, CatA, Irp9 and AroG*. MA content in mature senesced dried stems of nahG-catA-1.2 and nahG-catA-1.2× Irp9 transgenic lines. Error bars represent the SE from four biological replicates (n=4). Asterisks indicate significant differences from the nahG-catA-1.2 line using the unpaired Student's t-test (*P<0.05).
Figure 5C:
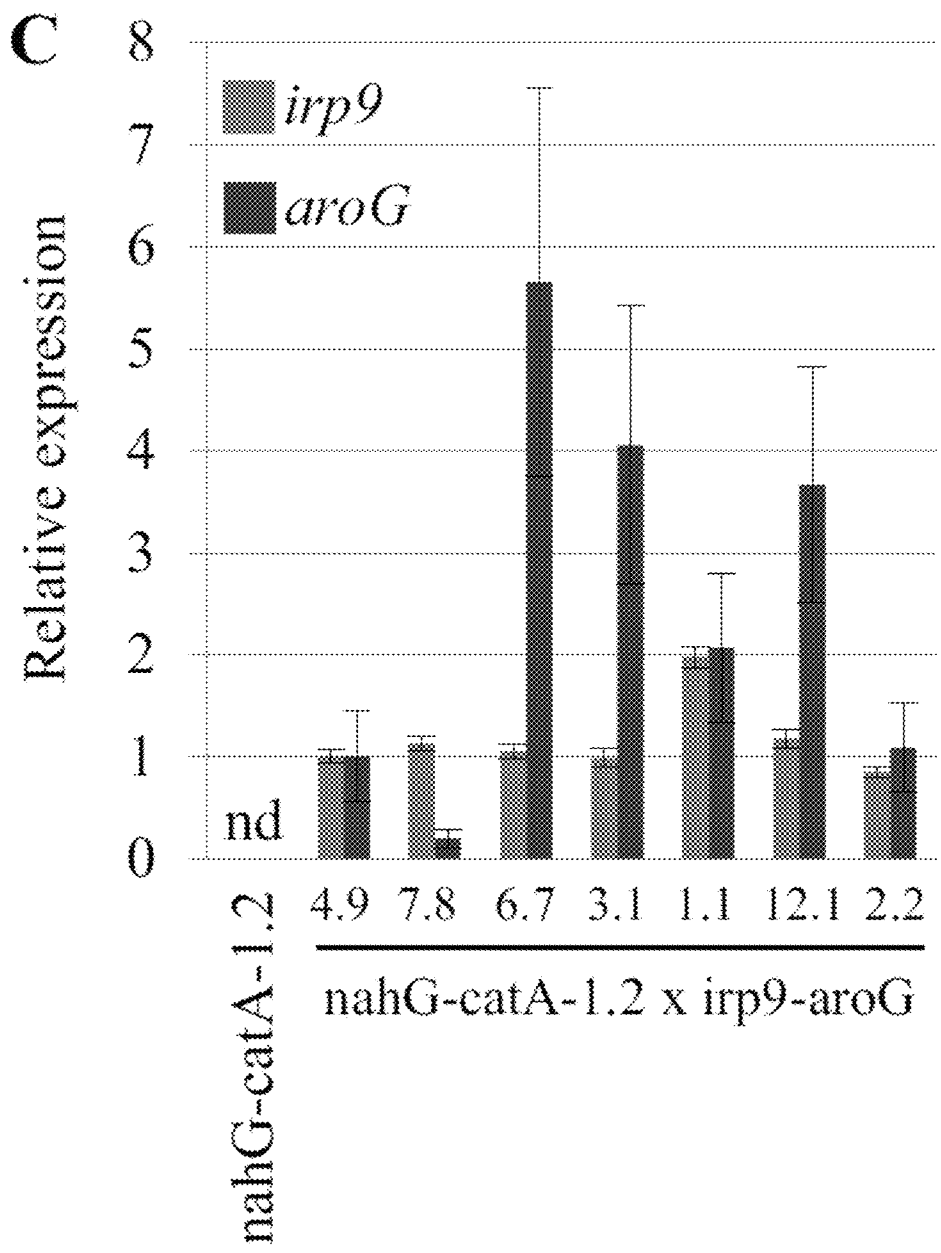
FIG. 5C. MA production in plants expressing bacterial NahG, CatA, Irp9 and AroG*. Detection by qRT-PCR of mRNA expression levels in stems from 5-week-old nahG-catA-1.2 and nahG-catA-1.2×Irp9-aroG transgenic lines. ACT2 is used as an internal control. Irp9 and aroG expression levels are normalized to 1 in line nahG-catA-1.2×Irp9-aroG 4.9 and were calculated relative to these values in the other lines. Error bars represent the SD from technical duplicates.
Figure 5D:
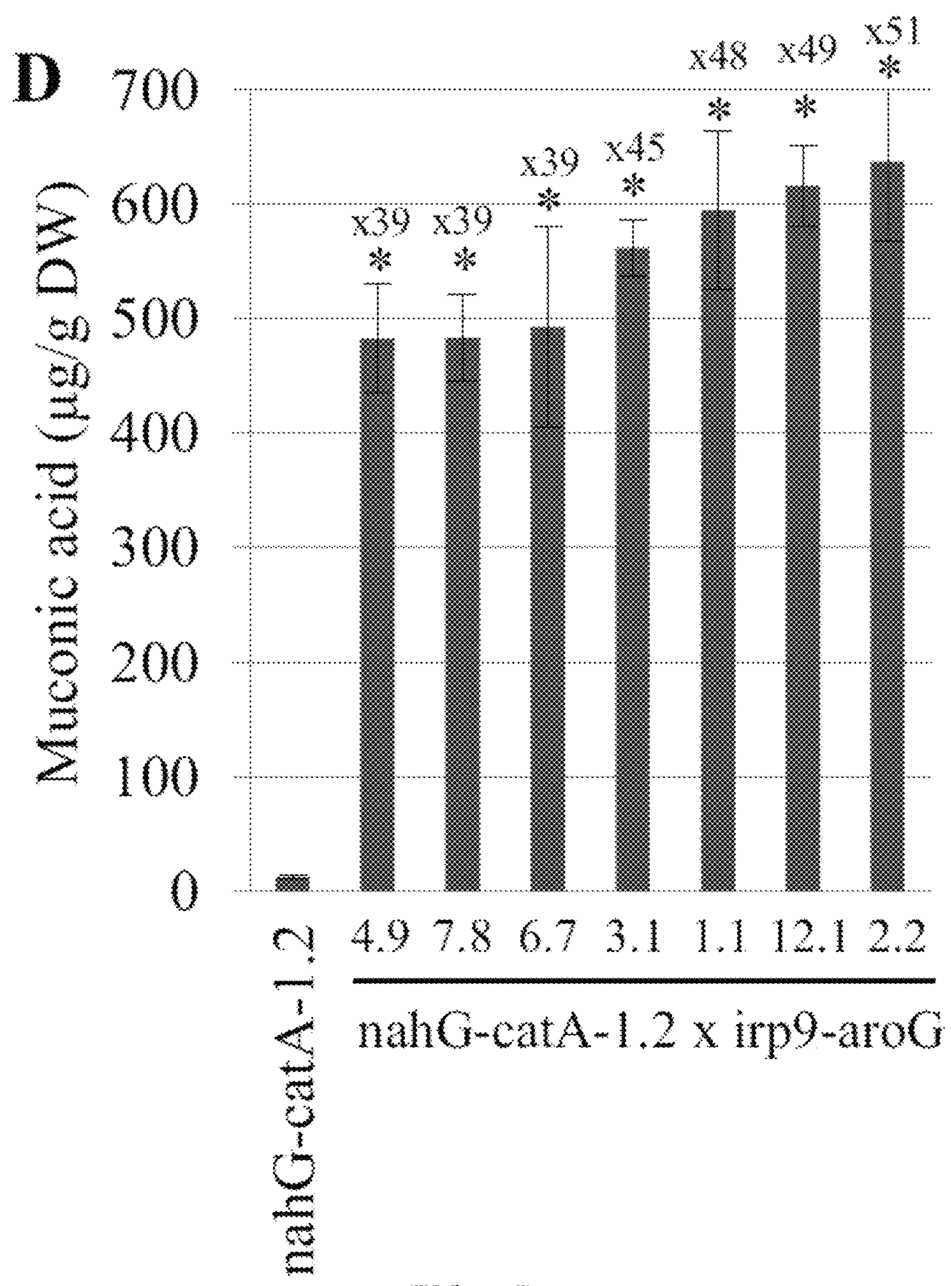
FIG. 5D. MA production in plants expressing bacterial NahG, CatA, Irp9 and AroG*. MA content in mature senesced dried stems of nahG-catA-1.2 and nahG-catA-1.2× irp9-aroG transgenic lines. Error bars represent the SE from four biological replicates (n=4). Asterisks indicate significant differences from the nahG-catA-1.2 line using the unpaired Student's t-test (*P<0.001).
Figure 7A:
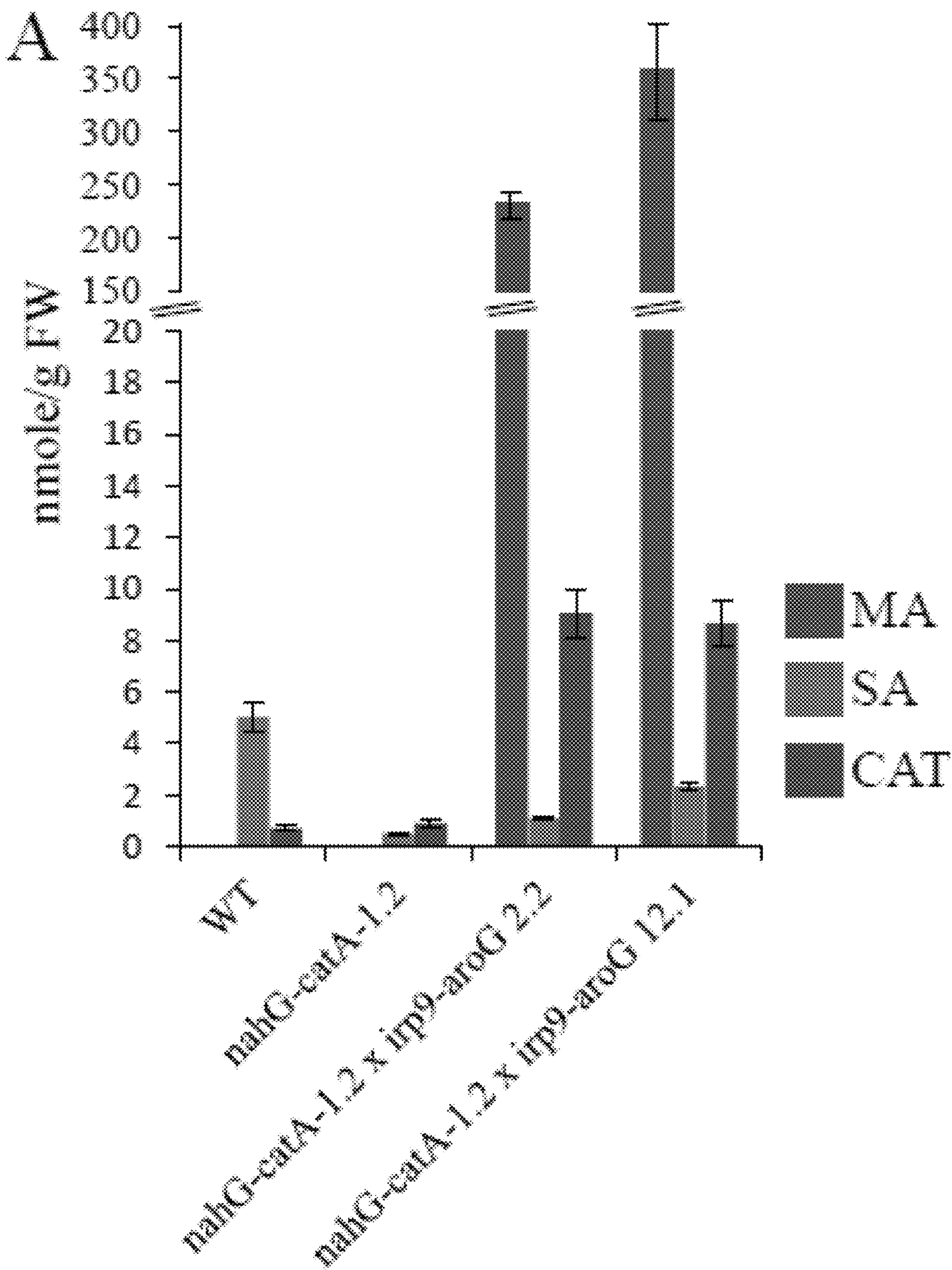
FIG. 7A. Salicylic acid (SA) and catechol (CAT) contents in stems of five-week-old wild type and muconic acid (MA) producing lines. Error bars represent the SE from four biological replicates (n=4).
Figure 7B:
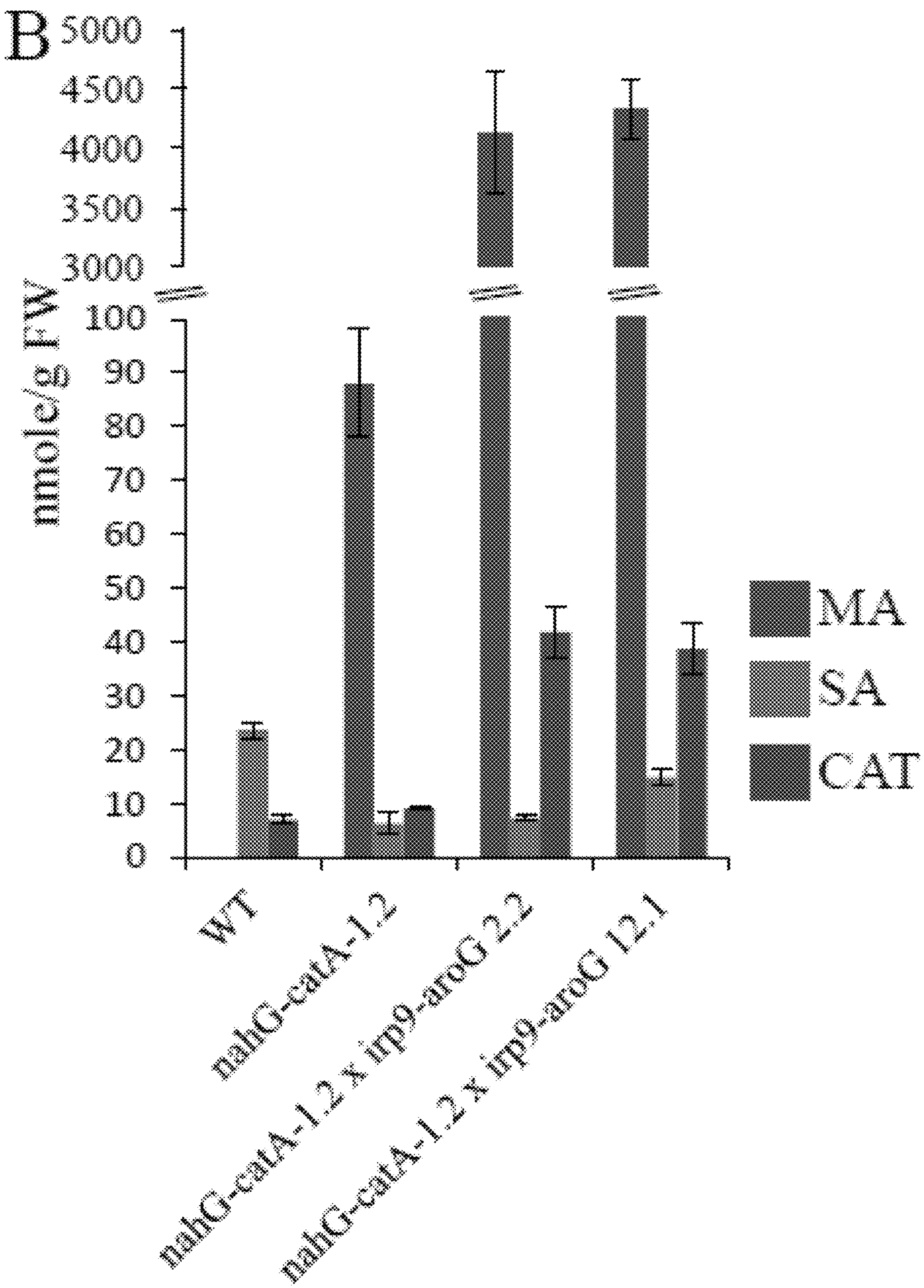
FIG. 7B. Salicylic acid (SA) and catechol (CAT) contents in stems of mature senesced wild type and muconic acid (MA) producing lines. Error bars represent the SE from four biological replicates (n=4).

To assess the effect of SA over-accumulation on MA production, the line nahG-catA-1.2 is transformed with the constructs used for expression of irp9 and for co-expression of irp9 and aroG* (FIG. 2B). First, several transgenic lines are selected that show expression of irp9 in the nahG-catA-1.2 background (FIG. 5A). Muconic acid content in stems of senesced nahG-catA-1.2×irp9 lines is increased 2- to 24-fold compared to the parental line (FIG. 5B). Second, several transgenic lines that show co-expression of irp9 and aroG* in the nahG-catA-1.2 genetic background are selected (FIG. 5C). In these lines, muconic acid content range between 483 and 637 μg/g DW, which represents a 39- to 51-fold increase compared to the values measured in the nahG-catA-1.2 parental line (FIG. 5D). These results demonstrate the positive effect of increasing the carbon flux through the SA route to enhance the production of MA in the proposed biosynthetic pathway. Furthermore, measurement of SA and catechol in two MA-producing lines reveals contents far below those of MA, suggesting that these two intermediates could limit MA biosynthesis (FIGS. 7A and 7B).

4. Discussion and Conclusions

This Example 1 demonstrates that bacterial catechol 1,2-dioxygenase (CatA) is functional in *Arabidopsis* plastids and thus can be exploited for the production of MA in plants. A biosynthetic route for catechol has been elegantly demonstrated in white campion flowers: it originates from phenylalanine and uses cinnamic acid, benzoic acid, and SA as intermediates (Akhtar and Pichersky, 2013). In this pathway, the biosynthetic genes involved in the steps for sequential conversion of benzoic acid into SA and catechol remain to be identified. Therefore, a plastid-targeted bacterial salicylate hydroxylase (NahG) is used in this work for the conversion of chorismate-derived SA into catechol. Gratifyingly, co-expression of NahG and CatA in plastids results in the production of MA, and MA titers can be further enhanced by increasing the carbon flux through SA biosynthetic pathway. Although the synthesis of SA from chorismate involves known plastidial isochorismate synthases, the plant enzyme(s) involved in the conversion of isochorismate into SA remain to be identified (Widhalm and Dudareva, 2015). Similarly, the identity and sub-cellular localization(s) of the enzymes that contribute to SA biosynthesis from cinnamic acid—an alternative SA pathway described in several plant species—have not all been elucidated (Dempsey et al., 2011). Therefore, a characterized bacterial bifunctional SA synthase (isochorismate synthase/isochorismate pyruvate lyase, Irp9) that has been previously validated in planta to enhance SA synthesis in *Arabidopsis* is targeted to plastids. Moreover, expression of plastid-targeted bacterial feedback-insensitive AroG enhanced SA production when co-expressed with Irp9, which confirms previous observations in *Arabidopsis* about the positive effect of AroG expression on the accumulation of metabolites derived from the shikimate pathway (Tzin et al., 2012). Considering low SA titers measured in transgenic *Arabidopsis* lines that produce MA (FIGS. 7A and 7B), additional engineering to enhance carbon flux through SA in these lines could improve MA titers. Whether the overexpression of other enzymes from the shikimate pathway (FIG. 2A, steps 2-7) would further increase the SA pool remains to be investigated. Similarly, the enolase responsible for the synthesis of phosphoenolpyruvate (FIG. 2A, step 1) could be targeted to increase SA content via the shikimate pathway since its overexpression was shown to drive carbon flux towards aromatic amino acid biosynthesis in tomato (Zhang et al., 2015). Specifically, the lack of correlation observed between aroG expression levels and SA (FIG. 4C-D) or MA (FIG. 5C-D) titers in our engineered plants suggests that one of the two aroG substrates could become limiting (FIG. 2A). Ultimately, since this MA biosynthetic route is confined to plastids, a trapping of SA inside plastids should be considered to avoid leak of this precursor, which could be achieved by downregulating known SA plastid exporters (Serrano et al., 2013).

Figure 8:
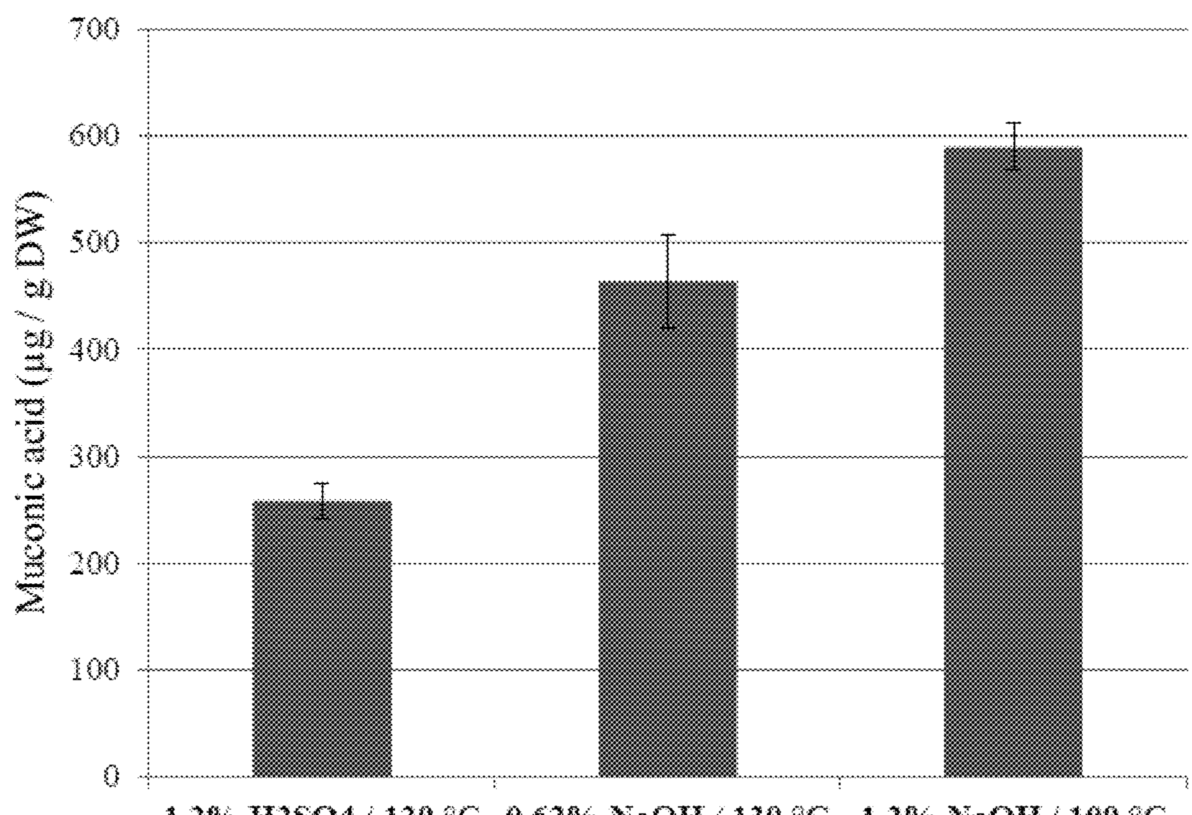
FIG. 8. Release of muconic acid from *Arabidopsis* biomass (line nahG-catA 1.2×irp9-aroG 2.2) upon treatments with dilute acid (1.2% w/w H2SO4) or dilute alkaline (0.62% w/w or 1.2% w/w NaOH) at different temperatures and using 10% (w/w) biomass loadings. Error bars represent the SD from three technical replicates.

More generally, certain crops engineered for reduced biomass recalcitrance and enhanced digestibility overproduce SA (Gallego-Giraldo et al., 2011), making them ideal genetic backgrounds for the production of both fermentable sugars and value-added MA Likewise, bioenergy *Populus* species (e.g., Salicaceae family) known to accumulate extremely high amounts of endogenous SA and SA-derived metabolites (up to 10% leaf dry weight) would represent adequate plant chassis for MA bioproduction (Lindroth and Hwang, 1996, Morse et al., 2007). In addition, it is anticipated that bioenergy crops engineered for MA accumulation can serve as compatible feedstock for MA-producing microbial strains able to grow on lignin-enriched streams derived from lignocellulosic biomass (Vardon et al., 2015, Rodriguez et al., 2017). Because such streams are generated with high solids loadings (>10% w/v), their enrichment with MA could be achieved using biomass containing MA. As an illustration, biomass containing 5% MA DW could potentially generate streams with 5 g/L MA (at 10% w/v biomass loading), a value similar to the best titers accomplished using engineered microbes and glucose as carbon source (Johnson et al., 2016). In this scenario, the MA titer reported for *Arabidopsis* (0.64 mg/g DW) would need to be improved by less than two orders of magnitude. More research will be needed to determine the optimal biomass pretreatment conditions for the release of MA. Preliminary study indicates that optimal dilute alkaline biomass pretreatments used to generate lignin-rich fractions for downstream biological upgrading (Karp et al., 2014) can efficiently release MA from biomass of the engineered *Arabidopsis* plants (FIG. 8). On the other hand, lower amount of MA is recovered when biomass was treated with dilute acid, possibly due to the cyclization of MA into muconolactone under these conditions (Carraher et al., 2017).

Figure 9:
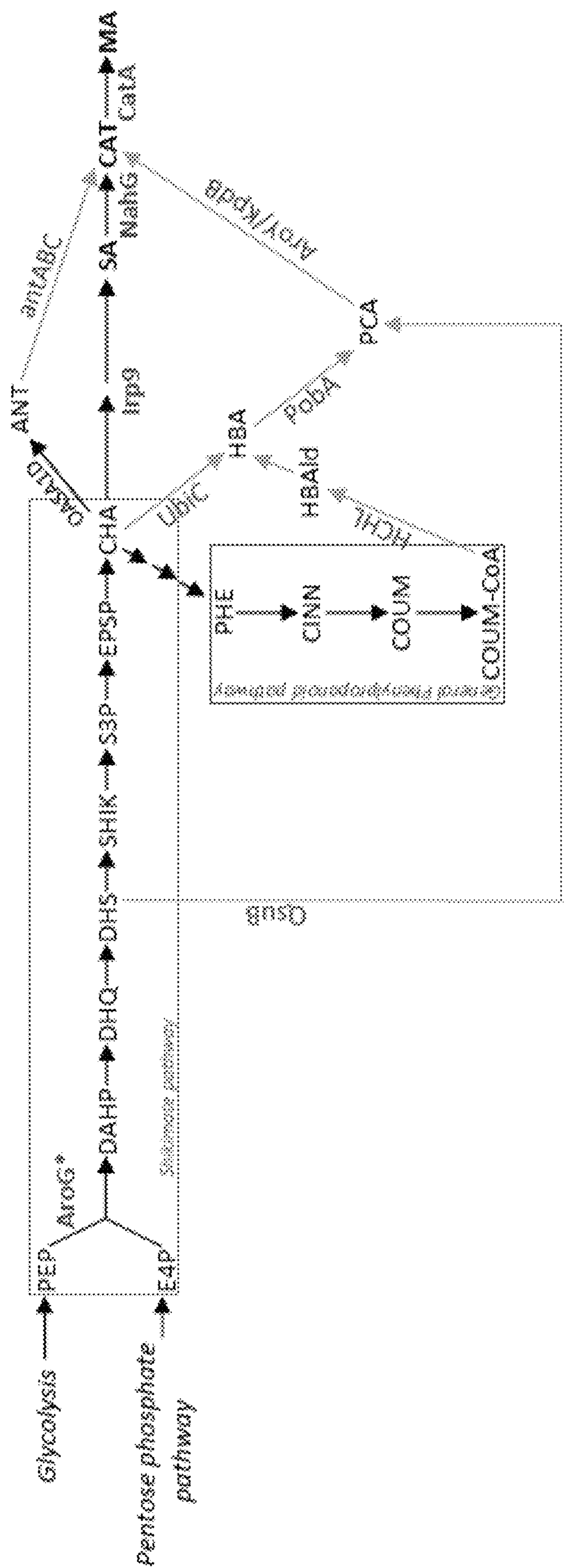
FIG. 9. Possible metabolic routes for the production of muconic acid (MA) in plants. Biosynthetic enzymes used in this work are indicated in purple. Bacterial enzymes belonging to alternative MA biosynthetic routes and whose functional expression in plants has been demonstrated are indicated in red. These are: antABC, anthranilate dioxygenase; AroY/KpdB, protocatechuate decarboxylase; HCHL, hydroxycinnamoyl-CoA hydratase-lyase; PobA, 4-hydroxybenzoate hydroxylase; QsuB, 3-dehydroshikimate dehydratase; UbiC, chorismate pyruvate lyase (Eudes et al., 2012; 2015; 2016, Shih et al., 2016; Wu et al., 2017). Expression of feedback-resistant anthranilate synthase alpha subunit (OASAD1) redirects carbon flux through anthranilate (ANT) (Ishihara et al., 2006; Last and Fink, 1988). Abbreviations are: CINN, cinnamate; COUM, p-coumarate; COUM-CoA, p-coumaroyl-CoA; HBA, 4-hydroxybenzoate; PCA, protocatechuate; PHE, phenylalanine. Refer to FIGS. 2A and 2B for other abbreviations.

As complementary approaches to the strategy presented in this work, the synthesis of catechol towards MA production could be achieved from alternate precursors such as anthranilate, protocatechuate, or 4-hydroxybenzoate as previously achieved in microorganisms (Kruyer and Peralta-Yahya, 2017). For this purpose, preliminary work conducted in tobacco validated that both anthranilate 1,2-dioxygenase and protocatechuate decarboxylase can be functionally expressed in plastids for the synthesis of catechol from anthranilate and protocatechuate, respectively (Shih et al., 2016a). In addition, previous engineering strategies in *Arabidopsis* have demonstrated the overproduction of anthranilate, protocatechuate, and 4-hydroxybenzoate from chorismate (Eudes et al., 2016, Ishihara et al., 2006, Last and Fink, 1988). Since protocatechuate and 4-hydroxybenzoate synthesis can also be accomplished from the precursors 3-dehydroshikimate and p-coumaroyl-CoA, respectively (Eudes et al., 2012, Eudes et al., 2016, Wu et al., 2017), production of high MA titers in plants could be envisioned by stacking branched biosynthetic routes that use diverse intermediates and products of the shikimate pathway (FIG. 9), and assisted by the use of synthetic promoters to optimize and synchronize the expression of multiple biosynthetic genes (Shih et al., 2016b).

REFERENCES CITED

Akhtar, T. A., Pichersky, E., 2013. Veratrole biosynthesis in white campion. Plant Physiol. 162, 52-62.

Barton, N., Horbal, L., Starck, S., Kohlstedt, M., Luzhetskyy, A., Wittmann, C., 2017. Enabling the valorization of guaiacol-based lignin: integrated chemical and biochemical production of cis,cis-muconic acid using metabolically engineered Amycolatopsis sp ATCC 39116. Metab. Eng. 2017.12.001.

Bechtold, N., Pelletier, G., 1998. In planta *Agrobacterium*-mediated transformation of adult *Arabidopsis thaliana* plants by vacuum infiltration. Methods Mol. Biol. 82, 259-266.

Bell-Lelong, D. A., Cusumano, J. C., Meyer, K., Chapple, C., 1997. Cinnamate-4-hydroxylase expression in *Arabidopsis*. Regulation in response to development and the environment. Plant Physiol. 113, 729-738.

Börnke, F., Broer, I., 2010. Tailoring plant metabolism for the production of novel polymers and platform chemicals. Curr. Opin. Plant Biol. 13, 354-362.

Carraher, J. M., Pfennig, T., Rao, R. G., Shanks, B. H., Tessonnier, J.-P., 2017. Cis,cis-Muconic acid isomerization and catalytic conversion to biobased cyclic-C6-1,4-diacid monomers. Green Chem. 19, 3042-3050.

Dempsey, D. A., Vlot, A. C., Wildermuth, M. C., Klessig, D. F., 2011. Salicylic acid biosynthesis and metabolism. *Arabidopsis* Book 9, e0156.

Do, C. T., Pollet, B., Thévenin, J., Sibout, R., Denoue, D., Barrière, Y., Lapierre, C., Jouanin, L., 2007. Both caffeoyl Coenzyme A 3-O-methyltransferase 1 and caffeic acid O-methyltransferase 1 are involved in redundant functions for lignin, flavonoids and sinapoyl malate biosynthesis in *Arabidopsis*. Planta 226, 1117-1129.

Eudes, A., George, A., Mukerjee, P., Kim, J. S., Pollet, B., Benke, P. I., Yang, F., Mitra, P., Sun, L., Cetinkol, O. P., Chabout, S., Mouille, G., Soubigou-Taconnat, L., Balzergue, S., Singh, S., Holmes, B. M., Mukhopadhyay, A., Keasling, J. D., Simmons, B. A., Lapierre, C., Ralph, J., Loqué, D., 2012. Biosynthesis and incorporation of side-chain-truncated lignin monomers to reduce lignin polymerization and enhance saccharification. Plant Biotechnol. J. 10, 609-620.

Eudes, A., Sathitsuksanoh, N., Baidoo, E. E., George, A., Liang, Y., Yang, F., Singh, S., Keasling, J. D., Simmons, B. A., Loqué, D., 2015. Expression of a bacterial 3-dehydroshikimate dehydratase reduces lignin content and improves biomass saccharification efficiency. Plant Biotechnol. J. 13, 1241-1250.

Eudes, A., Pereira, J. H., Yogiswara, S., Wang, G., Teixeira Benites, V., Baidoo, E. E., Lee, T. S., Adams, P. D., Keasling, J. D., Loqué, D., 2016. Exploiting the substrate promiscuity of hydroxycinnamoyl-CoA: shikimate hydroxycinnamoyl transferase to reduce lignin. Plant Cell Physiol. 57, 568-579.

Farré, G., Blancquaert, D., Capell, T., Van Der Straeten, D., Christou, P., Zhu, C., 2014. Engineering complex metabolic pathways in plants. Annu. Rev. Plant Biol. 65, 187-223.

Friedrich, L., Vernooij, B., Gaffney, T., Morse, A., Ryals, J., 1995. Characterization of tobacco plants expressing a bacterial salicylate hydroxylase gene. Plant Mol. Biol. 29, 959-968.

Gallego-Giraldo, L., Escamilla-Trevino, L., Jackson, L. A., Dixon, R. A., 2011. Salicylic acid mediates the reduced growth of lignin down-regulated plants. Proc. Natl. Acad. Sci. USA. 108, 20814-20819.

Haushalter, R. W., Phelan, R. M., Hoh, K. M., Su, C., Wang, G., Baidoo, E. E., Keasling, J. D., 2017. Production of odd-carbon dicarboxylic acids in *Escherichia coli* using an engineered biotin-fatty acid biosynthetic pathway. J. Am. Chem. Soc. 139, 4615-4618.

Ishihara, A., Asada, Y., Takahashi, Y., Yabe, N., Komeda, Y., Nishioka, T., Miyagawa, H., Wakasa, K., 2006. Metabolic changes in *Arabidopsis thaliana* expressing the feedback-resistant anthranilate synthase alpha subunit gene OASA1D. Phytochemistry 67, 2349-2362.

Johnson, C. W., Salvachúa, D., Khanna, P., Smith, H., Peterson, D. J., Beckham, G. T., 2016. Enhancing muconic acid production from glucose and lignin-derived aromatic compounds via increased protocatechuate decarboxylase activity. Metab. Eng. Commun. 3, 111-119.

Johnson, C. W., Abraham, P. E., Linger, J. G., Khanna, P., Hettich, R. L., Beckham, G. T., 2017. Eliminating a global regulator of carbon catabolite repression enhances the conversion of aromatic lignin monomers to muconate in *Pseudomonas putida* KT2440. Metab. Eng. Commun. 5, 19-25.

Karp, E. M., Donohoe, B. S., O'Brien, M. H., Ciesielski, P. N., Mittal, A., Biddy, M. J., Beckham, G. T., 2014. Alkaline pretreatment of corn stover: bench-scale fractionation and stream characterization. ACS Sustain. Chem. Eng. 2, 1481-1491.

Kruyer, N. S., Peralta-Yahya, P., 2017. Metabolic engineering strategies to bio-adipic acid production. Curr. Opin. Biotechnol. 45, 136-143.

Last, R. L., Fink, G. R., 1988. Tryptophan-requiring mutants of the plant *Arabidopsis thaliana*. Science 240, 305-310.

Lebrun, M., Leroux, B., Sailland, A., 1992. Gène chimère pour la transformation des plantes. European patent application. Patent Application No. EP 508909A1.

Lindroth, R. L., Hwang, S. Y., 1996. Diversity, redundancy and multiplicity in chemical defense systems of aspen. Recent Adv. Phytochem. 30, 25-56.

Livak, K. J., Schmittgen, T. D., 2011. Analysis of relative gene expression data using realtime quantitative PCR and the 2(-Delta Delta C(T)) method. Methods 25, 402-408.

Maeda, H., Dudareva, N., 2012. The shikimate pathway and aromatic amino acid biosynthesis in plants. Annu. Rev. Plant Biol. 63,73-105.

Matthiesen, J. E., Carraher, J. M., Vasiliu, M., Dixon, D. A., Tessonnier, J.-P., 2016. Electrochemical conversion of muconic acid to biobased diacid monomers. ACS Sustain. Chem. Eng. 4, 3575-3585.

Morse, A. M., Tschaplinski, T. J., Dervinis, C., Pijut, P. M., Schmelz, E. A., Day, W., Davis, J. M., 2007. Salicylate and catechol levels are maintained in nahG transgenic poplar. Phytochemistry 68, 2043-2052.

Persson, S., Caffall, K. H., Freshour, G., Hilley, M. T., Bauer, S., Poindexter, P., Hahn, M. G., Mohnen, D., Somerville, C., 2007. The *Arabidopsis* irregularxylem8 mutant is deficient in glucuronoxylan and homogalacturonan, which are essential for secondary cell wall integrity. Plant Cell. 19, 237-255.

Rodriguez, A., Salvachua, D., Katahira, R., Black, B. A., Cleveland, N. S., Reed, M., Smith, H., Baidoo, E. E. K., Keasling, J. D., Simmons, B. A., Beckham, G. T., Gladden, J. M., 2017. Base-catalyzed depolymerization of solid lignin-rich streams enables microbial conversion. ACS Sustain. Chem. Eng. 5, 8171-8180.

Serrano, M., Wang, B., Aryal, B., Garcion, C., Abou-Mansour, E., Heck, S., Geisler, M., Mauch, F., Nawrath, C., Métraux, J.P., 2013. Export of salicylic acid from the chloroplast requires the multidrug and toxin extrusion-like transporter EDS5. Plant Physiol. 162, 1815-1821.

Sha, J., 2003. The salicylic acid loop in plant defense. Curr. Opin. Plant Biol. 6,365-371.

Shih, P. M., Vuu, K., Eudes, A., Loqué, D., 2016a. Bioproduction of muconic acid in plants. International Conference on Plant Synthetic Biology and Bioengineering, Miami Beach, Fla. December 16-18.

Shih, P. M., Liang, Y., Loqué, D., 2016b. Biotechnology and synthetic biology approaches for metabolic engineering of bioenergy crops. Plant J. 87, 103-117.

Snell, K. D., Singh, V., Brumbley, S. M., 2015. Production of novel biopolymers in plants: recent technological advances and future prospects. Curr. Opin. Biotechnol. 32, 68-75.

Sonoki, T., Morooka, M., Sakamoto, K., Otsuka, Y., Nakamura, M., Jellison, J., Goodell, B., 2014. Enhancement of protocatechuate decarboxylase activity for the effective production of muconate from lignin-related aromatic compounds. J. Biotechnol. 192(Pt A), 71-77.

Sonoki, T., Takahashi, K., Sugita, H., Hatamura, M., Azuma, Y., Sato, T., Suzuki, S., Kamimura, N., Masai, E., 2017. Glucose-free cis,cis-muconic acid production via new metabolic designs corresponding to the heterogeneity of lignin. ACS Sustain. Chem. Eng.

Tzin, V., Malitsky, S., Ben Zvi, M. M., Bedair, M., Sumner, L., Aharoni, A., Galili, G., 2012. Expression of a bacterial feedback-insensitive 3-deoxy-D-arabino-heptulosonate 7-phosphate synthase of the shikimate pathway in *Arabidopsis* elucidates potential metabolic bottlenecks between primary and secondary metabolism. New Phytol. 194, 430-439.

Vaillancourt, F. H., Bolin, J. T., Eltis, L. D., 2006. The ins and outs of ring-cleaving dioxygenases. Crit. Rev. Biochem. Mol. Biol. 41, 241-267.

Vardon, D. R., Franden, M. A., Johnson, C. W., Karp, E. M., Guarnieri, M. T., Linger, J. G., Salm, M. J., Strathmann, T. J., Beckham, G. T., 2015. Adipic acid production from lignin. Energy Environ. Sci. 8, 617-628.

Vega-Sánchez, M. E., Loqué, D., Lao, J., Catena, M., Verhertbruggen, Y., Herter, T., Yang, F., Harholt, J., Eb,ert, B., Baidoo, E. E., Keasling, J. D., Scheller, H. V., Heazlewood, J. L., Ronald, P. C., 2015. Engineering temporal accumulation of a low recalcitrancepolysaccharide leads to increased C6 sugar content in plant cell walls. Plant Biotechnol. J. 13, 903-914.

Widhalm, J. R., Dudareva, N., 2015. A familiar ring to it: biosynthesis of plant benzoic acids. Mol. Plant 8, 83-97.

Wu, W., Dutta, T., Varman, A., Eudes, A., Manalansan, B., Loqué, D., Singh, S., 2017. Lignin valorization: two hybrid biochemical routes for the conversion of polymeric lignin into value-added chemicals. Sci. Rep. 7, 8420.

Xie, N. Z., Liang, H., Huang, R. B., Xu, P., 2014. Biotechnological production of muconic acid: current status and future prospects. Biotechnol. Adv. 32, 615-622.

Xue, L. J., Guo, W., Yuan, Y., Anino, E. O., Nyamdari, B., Wilson, M. C., Frost, C. J., Chen, H. Y., Babst, B. A., Harding, S. A., Tsai, C. J., 2013. Constitutively elevated salicylic acid levels alter photosynthesis and oxidative state but not growth in transgenic Populus. Plant Cell 25, 2714-2730.

Yang, F., Mitra, P., Zhang, L., Prak, L., Verhertbruggen, Y., Kim, J. S., Sun, L., Zheng, K., Tang, K., Auer, M., Scheller, H. V., Loqué, D., 2013. Engineering secondary cell wall deposition in plants. Plant Biotechnol. J. 11, 325-335.

Yuan, L., Grotewold, E., 2015. Metabolic engineering to enhance the value of plants as green factories. Metab. Eng. 27, 83-91.

Zhang, Y., Butelli, E., Alseekh, S., Tohge, T., Rallapalli, G., Luo, J., Kawar, P. G., Hill, L., Santino, A., Fernie, A. R., Martin, C., 2015. Multi-level engineering facilitates the production of phenylpropanoid compounds in tomato. Nat. Commun. 6, 8635.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A genetically modified plant or plant cell which endogenously produces salicyclic acid comprising a first nucleic acid encoding a plastid transit peptide linked to a heterologous salicylate hydroxylase (NahG), a second nucleic acid encoding a plastid transit peptide linked to a heterologous catechol 1,2-dioxygenase (CatA), which synthesize muconic acid (MA), a third nucleic acid encoding a plastid transit peptide linked to a heterologous bifunctional ISOCHA synthase/ISOCHA pyruvate lyase (Irp9) operatively linked to a promoter, and a fourth nucleic acid encoding a plastid transit peptide linked to a heterologous a feedback-resistant DAHP synthase (L175Q) (AroG*);

wherein the genetically modified plant or plant cell produces a MA titer with an at least 39-fold increase compared to a MA titer of a plant or plant cell modified only with the first nucleic acid encoding a plastid transit peptide linked to a heterologous salicylate hydroxylase (NahG), and a second nucleic acid encoding a plastid transit peptide linked to a heterologous catechol 1,2-dioxygenase (CatA), and the genetically modified plant or plant cell produces a MA titer of at least 483 μg/g DW; wherein the genetically modified plant cell or plant is of an Arabidopsis or Populus species.

2. The genetically modified plant or plant cell of claim 1, wherein the salicylate hydroxylase (NahG) is a bacterial salicylate hydroxylase (NahG).

3. The genetically modified plant or plant cell of claim 1, wherein the catechol 1,2-dioxygenase (CatA) is a bacterial catechol 1,2-dioxygenase (CatA).

4. The genetically modified plant or plant cell of claim 1, wherein the bifunctional ISOCHA synthase/ISOCHA pyruvate lyase (Irp9) is bacterial or Yersinia enterocolitica bifunctional ISOCHA synthase/ISOCHA pyruvate lyase (Irp9).

5. The genetically modified plant or plant cell of claim 1, wherein the feedback-resistant DAHP synthase (L175Q) (AroG*) is bacterial or *E. coli* DAHP synthase (AroG) that has a L175Q mutation which causes the AroG to be feedback resistant.

6. A method for producing a muconic acid comprising: (a) providing a genetically modified plant cell or plant of claim 1, and (b) growing or culturing the genetically modified plant cell or plant to produce a muconic acid;

wherein the genetically modified plant cell or plant produces a MA titer of at least 483 μg/g DW.

7. The genetically modified plant or plant cell of claim 1, wherein each plastid transit peptide is a plastid transit peptide from Arabidopsis ferredoxin2 (schl1), a plastid transit peptide from pea (*Pisum sativum*) ribulose-1,5-bisphosphate carboxylase small subunit (schl2), or a plastid transit peptide from sunflower (*Helianthus annuus*) ribulose-1,5-bisphosphate carboxylase small subunit (schl3).

8. The genetically modified plant or plant cell of claim 2, wherein the bacterial salicylate hydroxylase (NahG) is a *Pseudomonas* salicylate hydroxylase (NahG).

9. The genetically modified plant or plant cell of claim 3, wherein the bacterial catechol 1,2-dioxygenase (CatA) is a *Pseudomonas* catechol 1,2-dioxygenase (CatA).

10. The genetically modified plant or plant cell of claim 4, wherein the bacterial bifunctional ISOCHA synthase/ISOCHA pyruvate lyase (Irp9) is a *Yersinia enterocolitica* bifunctional ISOCHA synthase/ISOCHA pyruvate lyase (Irp9).

11. The genetically modified plant or plant cell of claim 5, wherein the bacterial feedback-resistant DAHP synthase (L175Q) (AroG*) is a *E. coli* DAHP synthase (AroG) that has a L175Q mutation.

12. The method of claim 6, wherein the genetically modified plant or plant cell further comprises a third nucleic acid encoding a heterologous bifunctional ISOCHA synthase/ISOCHA pyruvate lyase (Irp9) operatively linked to a promoter, and a fourth nucleic acid encoding a heterologous a feedback-resistant DAHP synthase (L175Q) (AroG*) operatively linked to a promoter.

13. The method of claim 6, wherein the salicylate hydroxylase (NahG) is a bacterial salicylate hydroxylase (NahG).

14. The method of claim 6, wherein the catechol 1,2-dioxygenase (CatA) is a bacterial catechol 1,2-dioxygenase (CatA).

15. The method of claim 12, wherein the bifunctional ISOCHA synthase/ISOCHA pyruvate lyase (Irp9) is bacterial or *Yersinia enterocolitica* bifunctional ISOCHA synthase/ISOCHA pyruvate lyase (Irp9).

16. The method of claim 12, wherein the feedback-resistant DAHP synthase (L175Q) (AroG*) is bacterial or *E. coli* DAHP synthase (AroG) that has a L175Q mutation which causes the AroG to be feedback resistant.

17. The method of claim 12, wherein the first nucleic acid further encodes a plastid transit peptide linked to NahG, the second nucleic acid further encodes a plastid transit peptide linked to CatA, the third nucleic acid further encodes a plastid transit peptide linked to Irp9, and the fourth nucleic acid further encodes a plastid transit peptide linked to AroG*.

18. The method of claim 17, wherein each plastid transit peptide is a plastid transit peptide from Arabidopsis ferredoxin2 (schl1), a plastid transit peptide from pea (*Pisum sativum*) ribulose-1,5-bisphosphate carboxylase small subunit (schl2), or a plastid transit peptide from sunflower (Helianthus annuus) ribulose-1,5-bisphosphate carboxylase small subunit (schl3).

19. The method of claim 6, further comprising (c) pretreating the plant cell or plant, and (d) converting the muconic acid into an adipic acid, terephthalic acid, and/or caprolactam.

20. The method of claim 6, wherein the genetically modified plant cell or plant produces 3500 to 4500 nmole MA/g FW.

21. The genetically modified plant or plant cell of claim 1, wherein the genetically modified plant cell or plant is of an *Arabidopsis* species.

22. The method of claim 6, wherein the genetically modified plant cell or plant is of an *Arabidopsis* species.

* * * * *

SEQUENCE LISTING

```
<160> NUMBER OF SEQ ID NOS: 22

<210> SEQ ID NO 1
<211> LENGTH: 434
<212> TYPE: PRT
<213> ORGANISM: Pseudomonas putida

<400> SEQUENCE: 1

Met Lys Asn Asn Lys Leu Gly Leu Arg Ile Gly Ile Val Gly Gly Gly
1               5                   10                  15

Ile Ser Gly Val Ala Leu Ala Leu Glu Leu Cys Arg Tyr Ser His Ile
            20                  25                  30

Gln Val Gln Leu Phe Glu Ala Ala Pro Ala Phe Gly Glu Val Gly Ala
        35                  40                  45

Gly Val Ser Phe Gly Pro Asn Ala Val Arg Ala Ile Val Gly Leu Gly
    50                  55                  60

Leu Gly Glu Ala Tyr Leu Gln Val Ala Asp Arg Thr Ser Glu Pro Trp
65                  70                  75                  80

Glu Asp Val Trp Phe Glu Trp Arg Arg Gly Ser Asp Ala Ser Tyr Leu
                85                  90                  95

Gly Ala Thr Ile Ala Pro Gly Val Gly Gln Ser Ser Val His Arg Ala
            100                 105                 110

Asp Phe Ile Asp Ala Leu Val Thr His Leu Pro Glu Gly Ile Ala Gln
        115                 120                 125

Phe Gly Lys Arg Ala Thr Gln Val Glu Gln Gln Gly Gly Glu Val Gln
    130                 135                 140

Val Leu Phe Thr Asp Gly Thr Glu Tyr Arg Cys Asp Leu Leu Ile Gly
145                 150                 155                 160

Ala Asp Gly Ile Lys Ser Ala Leu Arg Ser His Val Leu Glu Gly Gln
                165                 170                 175

Gly Leu Ala Pro Gln Val Pro Arg Phe Ser Gly Thr Cys Ala Tyr Arg
            180                 185                 190

Gly Met Val Asp Ser Leu His Leu Arg Glu Ala Tyr Arg Ala His Gly
        195                 200                 205
```

Ile Asp Glu His Leu Val Asp Val Pro Gln Met Tyr Leu Gly Leu Asp
210 215 220

Gly His Ile Leu Thr Phe Pro Val Arg Asn Gly Gly Ile Ile Asn Val
225 230 235 240

Val Ala Phe Ile Ser Asp Arg Ser Glu Pro Lys Pro Thr Trp Pro Ala
245 250 255

Asp Ala Pro Trp Val Arg Glu Ala Ser Gln Arg Glu Met Leu Asp Ala
260 265 270

Phe Ala Gly Trp Gly Asp Ala Ala Arg Ala Leu Leu Glu Cys Ile Pro
275 280 285

Ala Pro Thr Leu Trp Ala Leu His Asp Leu Ala Glu Leu Pro Gly Tyr
290 295 300

Val His Gly Arg Val Val Leu Ile Gly Asp Ala Ala His Ala Met Leu
305 310 315 320

Pro His Gln Gly Ala Gly Ala Gly Gln Gly Leu Glu Asp Ala Tyr Phe
325 330 335

Leu Ala Arg Leu Leu Gly Asp Thr Gln Ala Asp Ala Gly Asn Leu Ala
340 345 350

Glu Leu Leu Glu Ala Tyr Asp Asp Leu Arg Arg Pro Arg Ala Cys Arg
355 360 365

Val Gln Gln Thr Ser Trp Glu Thr Gly Glu Leu Tyr Glu Leu Arg Asp
370 375 380

Pro Val Val Gly Ala Asn Glu Gln Leu Leu Gly Glu Asn Leu Ala Thr
385 390 395 400

Arg Phe Asp Trp Leu Trp Asn His Asp Leu Asp Thr Asp Leu Ala Glu
405 410 415

Ala Arg Ala Arg Leu Gly Trp Glu His Gly Gly Gly Gly Ala Leu Arg
420 425 430

Gln Gly

<210> SEQ ID NO 2
<211> LENGTH: 311
<212> TYPE: PRT
<213> ORGANISM: Pseudomonas putida

<400> SEQUENCE: 2

Met Thr Val Lys Ile Ser His Thr Ala Asp Ile Gln Ala Phe Phe Asn
1 5 10 15

Arg Val Ala Gly Leu Asp His Ala Glu Gly Asn Pro Arg Phe Lys Gln
20 25 30

Ile Ile Leu Arg Val Leu Gln Asp Thr Ala Arg Leu Ile Glu Asp Leu
35 40 45

Glu Ile Thr Glu Asp Glu Phe Trp His Ala Val Asp Tyr Leu Asn Arg
50 55 60

Leu Gly Gly Arg Asn Glu Ala Gly Leu Leu Ala Ala Gly Leu Gly Ile
65 70 75 80

Glu His Phe Leu Asp Leu Leu Gln Asp Ala Lys Asp Ala Glu Ala Gly
85 90 95

Leu Gly Gly Gly Thr Pro Arg Thr Ile Glu Gly Pro Leu Tyr Val Ala
100 105 110

Gly Ala Pro Leu Ala Gln Gly Glu Ala Arg Met Asp Asp Gly Thr Asp
115 120 125

Pro Gly Val Val Met Phe Leu Gln Gly Gln Val Phe Asp Ala Asp Gly
130 135 140

```
Lys Pro Leu Ala Gly Ala Thr Val Asp Leu Trp His Ala Asn Thr Gln
145                 150                 155                 160

Gly Thr Tyr Ser Tyr Phe Asp Ser Thr Gln Ser Glu Phe Asn Leu Arg
                165                 170                 175

Arg Arg Ile Ile Thr Asp Ala Glu Gly Arg Tyr Arg Ala Arg Ser Ile
            180                 185                 190

Val Pro Ser Gly Tyr Gly Cys Asp Pro Gln Gly Pro Thr Gln Glu Cys
        195                 200                 205

Leu Asp Leu Leu Gly Arg His Gly Gln Arg Pro Ala His Val His Phe
    210                 215                 220

Phe Ile Ser Ala Pro Gly His Arg His Leu Thr Thr Gln Ile Asn Phe
225                 230                 235                 240

Ala Gly Asp Lys Tyr Leu Trp Asp Asp Phe Ala Tyr Ala Thr Arg Asp
                245                 250                 255

Gly Leu Ile Gly Glu Leu Arg Phe Val Glu Asp Ala Ala Ala Ala Arg
            260                 265                 270

Asp Arg Gly Val Gln Gly Glu Arg Phe Ala Glu Leu Ser Phe Asp Phe
        275                 280                 285

Arg Leu Gln Gly Ala Lys Ser Pro Asp Ala Glu Ala Arg Ser His Arg
    290                 295                 300

Pro Arg Ala Leu Gln Glu Gly
305                 310
```

<210> SEQ ID NO 3
<211> LENGTH: 434
<212> TYPE: PRT
<213> ORGANISM: Yersinia enterocolitica

<400> SEQUENCE: 3

```
Met Lys Ile Ser Glu Phe Leu His Leu Ala Leu Pro Glu Glu Gln Trp
1               5                   10                  15

Leu Pro Thr Ile Ser Gly Val Leu Arg Gln Phe Ala Glu Glu Glu Cys
            20                  25                  30

Tyr Val Tyr Glu Arg Pro Pro Cys Trp Tyr Leu Gly Lys Gly Cys Gln
        35                  40                  45

Ala Arg Leu His Ile Asn Ala Asp Gly Thr Gln Ala Thr Phe Ile Asp
    50                  55                  60

Asp Ala Gly Glu Gln Lys Trp Ala Val Asp Ser Ile Ala Asp Cys Ala
65                  70                  75                  80

Arg Arg Phe Met Ala His Pro Gln Val Lys Gly Arg Arg Val Tyr Gly
                85                  90                  95

Gln Val Gly Phe Asn Phe Ala Ala His Ala Arg Gly Ile Ala Phe Asn
            100                 105                 110

Ala Gly Glu Trp Pro Leu Leu Thr Leu Thr Val Pro Arg Glu Glu Leu
        115                 120                 125

Ile Phe Glu Lys Gly Asn Val Thr Val Tyr Ala Asp Ser Ala Asp Gly
    130                 135                 140

Cys Arg Arg Leu Cys Glu Trp Val Lys Glu Ala Ser Thr Thr Thr Gln
145                 150                 155                 160

Asn Ala Pro Leu Ala Val Asp Thr Ala Leu Asn Gly Glu Ala Tyr Lys
                165                 170                 175

Gln Gln Val Ala Arg Ala Val Ala Glu Ile Arg Arg Gly Glu Tyr Val
            180                 185                 190

Lys Val Ile Val Ser Arg Ala Ile Pro Leu Pro Ser Arg Ile Asp Met
```

```
        195                 200                 205

Pro Ala Thr Leu Leu Tyr Gly Arg Gln Ala Asn Thr Pro Val Arg Ser
    210                 215                 220

Phe Met Phe Arg Gln Glu Gly Arg Glu Ala Leu Gly Phe Ser Pro Glu
225                 230                 235                 240

Leu Val Met Ser Val Thr Gly Asn Lys Val Val Thr Glu Pro Leu Ala
                245                 250                 255

Gly Thr Arg Asp Arg Met Gly Asn Pro Glu His Asn Lys Ala Lys Glu
            260                 265                 270

Ala Glu Leu Leu His Asp Ser Lys Glu Val Leu Glu His Ile Leu Ser
        275                 280                 285

Val Lys Glu Ala Ile Ala Glu Leu Glu Ala Val Cys Leu Pro Gly Ser
    290                 295                 300

Val Val Val Glu Asp Leu Met Ser Val Arg Gln Arg Gly Ser Val Gln
305                 310                 315                 320

His Leu Gly Ser Gly Val Ser Gly Gln Leu Ala Glu Asn Lys Asp Ala
                325                 330                 335

Trp Asp Ala Phe Thr Val Leu Phe Pro Ser Ile Thr Ala Ser Gly Ile
            340                 345                 350

Pro Lys Asn Ala Ala Leu Asn Ala Ile Met Gln Ile Glu Lys Thr Pro
        355                 360                 365

Arg Glu Leu Tyr Ser Gly Ala Ile Leu Leu Leu Asp Asp Thr Arg Phe
    370                 375                 380

Asp Ala Ala Leu Val Leu Arg Ser Val Phe Gln Asp Ser Gln Arg Cys
385                 390                 395                 400

Trp Ile Gln Ala Gly Ala Gly Ile Ile Ala Gln Ser Thr Pro Glu Arg
                405                 410                 415

Glu Leu Thr Glu Thr Arg Glu Lys Leu Ala Ser Ile Ala Pro Tyr Leu
            420                 425                 430

Met Val


<210> SEQ ID NO 4
<211> LENGTH: 350
<212> TYPE: PRT
<213> ORGANISM: Escherichia coli

<400> SEQUENCE: 4

Met Asn Tyr Gln Asn Asp Asp Leu Arg Ile Lys Glu Ile Lys Glu Leu
1               5                   10                  15

Leu Pro Pro Val Ala Leu Leu Glu Lys Phe Pro Ala Thr Glu Asn Ala
            20                  25                  30

Ala Asn Thr Val Ala His Ala Arg Lys Ala Ile His Lys Ile Leu Lys
        35                  40                  45

Gly Asn Asp Asp Arg Leu Leu Val Val Ile Gly Pro Cys Ser Ile His
    50                  55                  60

Asp Pro Val Ala Ala Lys Glu Tyr Ala Thr Arg Leu Leu Ala Leu Arg
65                  70                  75                  80

Glu Glu Leu Lys Asp Glu Leu Glu Ile Val Met Arg Val Tyr Phe Glu
                85                  90                  95

Lys Pro Arg Thr Thr Val Gly Trp Lys Gly Leu Ile Asn Asp Pro His
            100                 105                 110

Met Asp Asn Ser Phe Gln Ile Asn Asp Gly Leu Arg Ile Ala Arg Lys
        115                 120                 125

Leu Leu Leu Asp Ile Asn Asp Ser Gly Leu Pro Ala Ala Gly Glu Phe
```

```
    130                 135                 140

Leu Asp Met Ile Thr Pro Gln Tyr Leu Ala Asp Leu Met Ser Trp Gly
145                 150                 155                 160

Ala Ile Gly Ala Arg Thr Thr Glu Ser Gln Val His Arg Glu Leu Ala
                165                 170                 175

Ser Gly Leu Ser Cys Pro Val Gly Phe Lys Asn Gly Thr Asp Gly Thr
            180                 185                 190

Ile Lys Val Ala Ile Asp Ala Ile Asn Ala Ala Gly Ala Pro His Cys
        195                 200                 205

Phe Leu Ser Val Thr Lys Trp Gly His Ser Ala Ile Val Asn Thr Ser
    210                 215                 220

Gly Asn Gly Asp Cys His Ile Ile Leu Arg Gly Gly Lys Glu Pro Asn
225                 230                 235                 240

Tyr Ser Ala Lys His Val Ala Glu Val Lys Glu Gly Leu Asn Lys Ala
                245                 250                 255

Gly Leu Pro Ala Gln Val Met Ile Asp Phe Ser His Ala Asn Ser Ser
            260                 265                 270

Lys Gln Phe Lys Lys Gln Met Asp Val Cys Ala Asp Val Cys Gln Gln
        275                 280                 285

Ile Ala Gly Gly Glu Lys Ala Ile Ile Gly Val Met Val Glu Ser His
    290                 295                 300

Leu Val Glu Gly Asn Gln Ser Leu Glu Ser Gly Glu Pro Leu Ala Tyr
305                 310                 315                 320

Gly Lys Ser Ile Thr Asp Ala Cys Ile Gly Trp Glu Asp Thr Asp Ala
                325                 330                 335

Leu Leu Arg Gln Leu Ala Asn Ala Val Lys Ala Arg Arg Gly
            340                 345                 350


<210> SEQ ID NO 5
<211> LENGTH: 6
<212> TYPE: PRT
<213> ORGANISM: Pseudomonas putida
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 5

Gly Xaa Gly Xaa Xaa Gly
1               5


<210> SEQ ID NO 6
<211> LENGTH: 9
<212> TYPE: PRT
<213> ORGANISM: Pseudomonas putida
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 6

His Gly Arg Xaa Xaa Leu Xaa Gly Asp
1               5
```

```
<210> SEQ ID NO 7
<211> LENGTH: 6
<212> TYPE: PRT
<213> ORGANISM: Pseudomonas putida
<220> FEATURE:
<221> NAME/KEY: misc_feature
<222> LOCATION: (5)..(5)
<223> OTHER INFORMATION: Xaa can be any naturally occurring amino acid

<400> SEQUENCE: 7

Arg Pro Ala His Xaa His
1               5


<210> SEQ ID NO 8
<211> LENGTH: 1530
<212> TYPE: DNA
<213> ORGANISM: Artificial Sequence
<220> FEATURE:
<223> OTHER INFORMATION: Codon-optimized nucleotide sequence encoding
      Irp9 from Yersinia enterocolitica

<400> SEQUENCE: 8

acaagtttgt acaaaaaagc aggcttcatg gcatcaacag cattatcatc cgctatcgtg     60

ggaacatcat tcattaggag gagtccagca ccaatcagtc ttagatcatt accttctgca    120

aacacacaat cacttttcgg tttgaaatct ggaaccgcta gaggtggaag ggttacagct    180

atggcaacct ataaggttat gaaaatcagt gaattcttgc atttggcact tccagaagag    240

caatggttgc ctactatctc cggtgtttta agacagttcg ctgaagagga atgttatgtg    300

tacgaaagac caccttgttg gtacttaggt aaaggatgcc aagctagact tcacatcaac    360

gcagatggta cccaagctac ttttatagat gacgcaggag aacagaaatg ggctgttgat    420

tctattgcag actgcgctag aaggttcatg gcacatccac aagttaaggg tagaagggtt    480

tatggtcaag tgggttttaa tttcgctgca cacgctagag gtatagcttt taatgctgga    540

gaatggccat tgttaactct tacagttcct agagaggaat tgattttcga gaagggtaat    600

gtgactgttt acgcagattc tgctgacgga tgtagaaggt tgtgcgagtg ggttaaggaa    660

gcttcaacta caacccaaaa tgcacctctt gctgttgata cagcattgaa cggtgaagct    720

tataagcaac aggttgctag agcagtggct gagatcagaa ggggagaata cgtgaaggtt    780

atcgtgtcta gagctatacc attgccttca aggatagata tgccagcaac ccttttgtat    840

ggtagacaag ctaatactcc tgttaggtct tttatgttca gacaggaggg tagggaagca    900

ttaggattct ctccagagct tgttatgtca gtgactggaa acaaagttgt gacagaacca    960

ttagctggta ccagagatag gatgggaaat cctgagcata acaaagcaaa ggaggctgaa   1020

ttacttcatg acagtaaaga ggttttagaa cacatacttt ccgtgaagga agcaattgct   1080

gagttggaag ctgtttgttt acctggttca gttgtggttg aagatttgat gagtgttaga   1140

caaaggggtt ccgtgcagca cttgggttct ggagtttcag gacaattagc tgaaaacaag   1200

gatgcatggg acgcttttac tgttcttttc ccaagtatta cagcatccgg tatccctaaa   1260

aatgctgcac ttaacgctat aatgcaaatt gagaagactc caagagaatt gtacagtgga   1320

gctatattgc ttcttgatga cacaagattc gatgctgcat tggttttaag gagtgtgttc   1380

caagactccc agagatgctg gatccaagca ggtgctggaa ttatcgctca gtcaacacct   1440

gagagagagt tgactgagac tagggagaaa ttagcatcaa tcgcacctta ccttatggtt   1500

tgagacccag ctttcttgta caaagtggtc                                    1530
```

<210> SEQ ID NO 9
<211> LENGTH: 2561
<212> TYPE: DNA
<213> ORGANISM: Artificial Sequence
<220> FEATURE:
<223> OTHER INFORMATION: Sequence containing the tg7 terminator from A. tumefaciens followed by the CCoAOMT1 promoter from A. thaliana containing an AvrII restriction site in its 3'-end and flanked with the Gateway attB4R and attB3R rec

<400> SEQUENCE: 9

```
gacaactttt ctatacaaag ttgactgact aactaggatg agctaagcta gctatatcat     60

caatttatgt attacacata atatcgcact cagtctttca tctacggcaa tgtaccagct    120

gatataatca gttattgaaa tatttctgaa tttaaacttg catcaataaa tttatgtttt    180

tgcttggact ataatacctg acttgttatt ttatcaataa atatttaaac tatatttctt    240

tcaagatggg aattaacatc tacaaattgc cttttcttat cgaccatgta ccccgggtac    300

caagcttctc gagagcagtg gatgagggaa gagaggatta agaggcgtag agattacatg    360

tgatgaatga tactatcttt tcttacaaac acattttcgt gtaattaaaa tttaatttgg    420

ttccaaagat tttaatcaaa agaagtttgg taaattgaaa caggcagaca taatttattg    480

taaagagttt ttatttattt attcatgacg ttgcttgatg gtgctttacc aattttcttc    540

tcctacgtta gatttttttc actttttttt ttggtgtttg taataaatgt gaaaaatgga    600

ccgtttaaaa acttaaagac gtttgattac tatataaagt aattgtttat aatagaaagt    660

taattgagac gtgaaatggt ataatattat tgtgtaacag ttgtgtacac gtagctctca    720

tgcagtttta gtggacccat atggcttgac ttgtattctg tttttgggct attaaagtcc    780

aaaacagaga cccctctcaa gcccttccta ttaatccatc tagctaatag aaactataaa    840

cgtgtcctct ctctcaatta aataagctag aaacatactc aaccattcgc attacgcact    900

tcatagcggt aggtttagat ttgtctaaaa tacttaaaaa aatttttgtc taagttgttg    960

tccgttacaa agtttttttc tttgtgacaa cttgacaaca ttgacaaata gaaaaataaa   1020

tttcgatgaa acctatgaaa tggctatggg cccaactaaa aagagtggga aattaaagat   1080

gggatggttc aagtgtatac ttcgaacttc cgacattagg gtcaaaggat ttttaaaagg   1140

caaccatttg ttccactttc tcgaacaaaa acgagccatt tattaatata tagtacggct   1200

gaattggttt tgttcgtcat tgtgtaaaca caaagtcatt cgaattatgt tagggtccgt   1260

tgataaatata gacggcccat cccacgcaca tattaagtgt tcaactccat agaatatcat   1320

atgggacact gtttttaatt tataatcacc atttaaaatg tttaaatgtt tatgcaaatt   1380

ggatggcttc ttcacacaac atttatttat tggcctttca ttccatcaaa gtaaaatagc   1440

ttttcaaata cattatactc tatactccta tacatgtaaa taaccatatg catatatatt   1500

tttttcaaat ataggtcaac gccatttaat ataattttaa aaaaatttgt tcggaaaata   1560

tcacatttct ttcactagac aagccttgtt accacacaat gtatcaatat gatctaaagg   1620

gcaaacgaaa gatcctgaca tgaaacgttt aattctcatt ttctccaaat tttatttttt   1680

atgtgaagta gataaattag tatatatata tatataccaa actagtgtgt tatgttatgg   1740

caaatgttat atcaattcga aggttccgct attgcaatat tcattaattt tttcatacca   1800

atactatttt tctttctctt ttattttgtt ttttaataaa taaaagaaat taaggatgat   1860

tagtaaggaa gtcgcctacc aagagattca cctaccacgg tacacttcaa caccgaagca   1920

gagttgttga atccactttt tattcccttc tctaatctct actcaccaag tctccacttt   1980

tttttctctt tattatatac atttaaatta tttaatatac gccaactaca tacatatcca   2040
```

```
gtgtaatttc tcgttacgtc acaccccttt cgtaatcgtc taatttcaga aaaatatcca   2100

gaggtttaaa tacatattcc catcattaaa tctagacata aacacatcat actcacaaaa   2160

tttggcagca aacagttact acagacccat aaatgaaaaa acgtattcac ttgttttcaa   2220

ttttcacata accacttccc tgagtttggt ctcaatttga ttgccccgcc gaggcattac   2280

tacgccaagt gcgattaagg tcccatacag tgtaacggga cccactataa gacagcgacc   2340

gaccaattgc gtgttaggag agtttcacca accccggacc ggtttttacc ggatataaca   2400

gaaccggtac gaaccggtct cattatcttc catcttcttt atatagacct catgccatgt   2460

gtgtgactca ccaagaaaaa cacaatcgtt taatctcacc caagaagaca aaaacacaga   2520

gagagaaaga gagagaaaca actttgtata ataaagttgt c                       2561
```

<210> SEQ ID NO 10
<211> LENGTH: 1372
<212> TYPE: DNA
<213> ORGANISM: Artificial Sequence
<220> FEATURE:
<223> OTHER INFORMATION: Codon-optimized nucleotide sequence encoding CatA from Pseudomonas

<400> SEQUENCE: 10

```
acaagtttgt acaaaaaagc aggcttcatg gcgagtatct ccagcagcgt tgcgacagtg     60

agcagaacag caccggcaca agcgaatatg gttgcaccgt ttacgggatt gaaaagtaat    120

gctgcgtttc caaccactaa aaaggccaat gatttctcga cactgccgtc caacggtggc    180

cgtgttcagt gtatgcaagt gtggccggct tatggaaaca aaaagtttga aactctgtct    240

taccttccgc ctttgtcaac aatggcgcct acggtcatga tggcatcttc agcaaccgcc    300

gtggctccat tccagggtct gaaaagcact gctagtcttc ctgtggctcg ccgttcttcc    360

cgctcgcttg gtaatgtttc taatggaggt cgtatcagat gcatgcagat gaccgtgaaa    420

atctcccaca ctgctgacat acaggcattc tttaacagag ttgctggatt agaccacgct    480

gaaggtaacc caaggttcaa gcaaattatc ttgagagttc ttcaggatac tgctaggtta    540

atcgaagatc ttgagataac agaagacgag ttctggcatg ctgtggatta tcttaataga    600

ttgggtggaa ggaacgaagc aggtttgtta gctgcaggac ttggtataga gcactttttg    660

gatcttttgc aagatgctaa agacgctgaa gcaggtttgg gtggtggtac tccaagaact    720

attgagggac ctttgtatgt tgctggtgca ccattagctc aaggagaagc aaggatggat    780

gacggaacag atcctggtgt tgtgatgttt ttacagggtc aggttttcga tgctgacgga    840

aagccacttg ctggtgcaac cgtggatttg tggcatgcta acacacaagg tacttattct    900

tacttcgatt ctacccagtc agaattcaat ttgagaagaa gaattattac tgatgctgag    960

ggaaggtata gagcaaggag tatcgttcct tccggatacg gttgtgatcc acaaggacct   1020

actcaggaat gcttagactt acttggaaga cacggtcaaa ggccagctca tgttcacttt   1080

ttcattagtg cacctggtca tagacactta actacacaga tcaatttcgc tggagataaa   1140

tatctttggg atgacttcgc ttacgcaact agagatggtt tgattggtga attaaggttt   1200

gttgaggatg ctgcagctgc aagagacagg ggagtgcaag gtgaaagatt cgctgagtta   1260

tcatttgatt tcagacttca gggtgcaaag tctccagacg ctgaagcaag atcacataga   1320

ccaagagctt tgcaagaggg atgacaccca acttttctat acaaagttgt ct           1372
```

<210> SEQ ID NO 11
<211> LENGTH: 1359

<212> TYPE: DNA
<213> ORGANISM: Artificial Sequence
<220> FEATURE:
<223> OTHER INFORMATION: Codon-optimized nucleotide sequence encoding NahG from Pseudomonas

<400> SEQUENCE: 11

```
acaactttgt ataataaagt tggcatgaaa aataataagt tgggtttgag aatcggtatc      60
gtgggtggtg gaatatcagg agtggcattg gcattggaat tgtgcaggta tagtcatatc     120
caagttcagt tatttgaggc tgcaccagct ttcggagaag ttggtgcagg agtgtccttt     180
ggtcctaatg cagttagagc tatagtgggt ttaggacttg gagaggcata tcttcaagtt     240
gctgacagga cctctgaacc ttgggaggat gtgtggttcg aatggagaag gggaagtgat     300
gcttcctact tgggtgcaac tattgctcca ggagttggac agtcttcagt gcatagagca     360
gactttatcg atgctttagt tactcacctt cctgaaggaa tagctcaatt cggtaaaaga     420
gcaacacagg tggagcaaca gggtggagaa gttcaagtgt tgtttactga tggtacagaa     480
tatagatgtg acttgttaat aggagctgat ggtattaaga gtgcacttag gtcccatgtt     540
ttggaaggac aaggtttagc tccacaggtg cctagattct ctggaacttg cgcttatagg     600
ggtatggttg attcattgca tttgagagag gcatacaggg ctcatggtat cgacgaacac     660
ttggttgatg tgccacaaat gtaccttgga ttggatggtc acattttaac atttcctgtt     720
agaaatggtg gaattatcaa cgttgtggct ttcatctctg acaggtcaga acctaaacct     780
acctggccag ctgatgcacc ttgggttaga gaggcttctc aaagggaaat gttggacgct     840
tttgcaggat ggggagatgc tgctagagct ttgttggaat gtataccagc acctacttta     900
tgggctcttc atgacttggc agaattacca ggatatgttc acggtagagt tgtgttgatt     960
ggagatgctg cacatgctat gttacctcac caaggagctg gtgcaggaca gggtcttgaa    1020
gatgcatact tcttggctag attacttgga gacacacaag ctgatgcagg taatcttgct    1080
gaattgttgg aggcttatga tgacttgaga aggccaagag cttgcagggt tcaacagacc    1140
tcatgggaaa ctggagagct ttacgaattg agagatcctg ttgtgggagc taatgagcaa    1200
cttttgggtg aaaacttagc aacaagattt gattggcttt ggaaccatga tttggacact    1260
gatttggctg aggcaagagc taggttggga tgggaacacg gtggaggtgg tgctttgaga    1320
cagggttgag acccagcttt cttgtacaaa gtggtctga                           1359
```

<210> SEQ ID NO 12
<211> LENGTH: 20
<212> TYPE: DNA
<213> ORGANISM: Artificial Sequence
<220> FEATURE:
<223> OTHER INFORMATION: PCR forward primer for Irp-9

<400> SEQUENCE: 12

```
tgtagaaggt tgtgcgagtg                                                  20
```

<210> SEQ ID NO 13
<211> LENGTH: 22
<212> TYPE: DNA
<213> ORGANISM: Artificial Sequence
<220> FEATURE:
<223> OTHER INFORMATION: PCR reverse primer for Irp-9

<400> SEQUENCE: 13

```
cttcacgtat tctccccttc tg                                               22
```

<210> SEQ ID NO 14
<211> LENGTH: 20
<212> TYPE: DNA
<213> ORGANISM: Artificial Sequence
<220> FEATURE:
<223> OTHER INFORMATION: Forward primer for CatA

<400> SEQUENCE: 14
ttgggatgac ttcgcttacg 20

<210> SEQ ID NO 15
<211> LENGTH: 20
<212> TYPE: DNA
<213> ORGANISM: Artificial Sequence
<220> FEATURE:
<223> OTHER INFORMATION: Reverse primer for CatA

<400> SEQUENCE: 15
ggagactttg caccctgaag 20

<210> SEQ ID NO 16
<211> LENGTH: 20
<212> TYPE: DNA
<213> ORGANISM: Artificial Sequence
<220> FEATURE:
<223> OTHER INFORMATION: Forward primer for nahG

<400> SEQUENCE: 16
caaagggaaa tgttggacgc 20

<210> SEQ ID NO 17
<211> LENGTH: 22
<212> TYPE: DNA
<213> ORGANISM: Artificial Sequence
<220> FEATURE:
<223> OTHER INFORMATION: Reverse primer for nahG

<400> SEQUENCE: 17
gcatctccaa tcaacacaac tc 22

<210> SEQ ID NO 18
<211> LENGTH: 20
<212> TYPE: DNA
<213> ORGANISM: Artificial Sequence
<220> FEATURE:
<223> OTHER INFORMATION: Forward primer for aroG

<400> SEQUENCE: 18
gatgtttgtg ctgacgtgtg 20

<210> SEQ ID NO 19
<211> LENGTH: 23
<212> TYPE: DNA
<213> ORGANISM: Artificial Sequence
<220> FEATURE:
<223> OTHER INFORMATION: Reverse primer for aroG

<400> SEQUENCE: 19
ttccctcaac taagtgactt tcc 23

<210> SEQ ID NO 20
<211> LENGTH: 23
<212> TYPE: DNA
<213> ORGANISM: Artificial Sequence
<220> FEATURE:
<223> OTHER INFORMATION: Forward primer for ACT2

-continued

```
<400> SEQUENCE: 20

ggtaacattg tgctcagtgg tgg                                          23


<210> SEQ ID NO 21
<211> LENGTH: 23
<212> TYPE: DNA
<213> ORGANISM: Artificial Sequence
<220> FEATURE:
<223> OTHER INFORMATION: Reverse primer for ACT2

<400> SEQUENCE: 21

aacgacctta atcttcatgc tgc                                          23


<210> SEQ ID NO 22
<211> LENGTH: 1282
<212> TYPE: DNA
<213> ORGANISM: Artificial Sequence
<220> FEATURE:
<223> OTHER INFORMATION: Codon-optimized nucleotide sequence encoding
      feedback-insensitive AroG (L175Q) from E. coli

<400> SEQUENCE: 22

acaactttgt ataataaagt tggccatggc ttctatgata tcctcttcag ctgtgactac     60

agtcagccgt gcttctacgg tgcaatcggc cgcggtggct ccattcggcg gcctcaaatc    120

catgactgga ttcccagtta agaaggtcaa cactgacatt acttccatta caagcaatgg    180

tggaagagta aagtgcatgc agatgaatta ccagaacgat gacttaagaa tcaaagaaat    240

taaagagttg ttaccacctg tggctctttt ggaaaaattc ccagcaactg agaatgctgc    300

aaacacagtt gctcatgcaa gaaaggctat tcacaaaatc ttgaagggta atgatgacag    360

gttacttgtt gtgatcggac catgctcaat acatgatcct gttgctgcaa aggaatacgc    420

tactagattg cttgcattga gggaagagtt aaaggatgaa cttgagattg ttatgagagt    480

gtacttcgag aaaccaagga ccactgttgg ttggaaggga cttatcaatg atcctcacat    540

ggacaactcc ttccaaatta atgatggttt gagaatcgct aggaaacttt tgcttgatat    600

taacgactca ggtttgccag ctgcaggaga atttttagat atgatcacac ctcagtactt    660

agctgacctt atgtcatggg gtgctatagg agcaagaaca accgaaagtc aagttcatag    720

ggagcaggct tccggtttgt cttgtccagt gggattcaaa aatggtactg atggaacaat    780

taaggttgct atagacgcaa ttaacgctgc aggtgctcct cattgttttc tttctgttac    840

aaaatgggga cactcagcaa tcgtgaatac cagtggtaac ggagattgcc atattatctt    900

gagaggtgga aaagaaccaa attattcagc taagcacgtt gcagaagtga aagagggttt    960

gaacaaggct ggattacctg cacaagttat gatcgatttc tctcatgcta actcctctaa   1020

gcaattcaag aaacagatgg atgtttgtgc tgacgtgtgc caacagatcg ctggtggaga   1080

aaaggctatt attggtgtta tggtggaaag tcacttagtt gagggaaatc aatcattaga   1140

aagtggagag cctcttgctt acggaaaatc tattaccgat gcatgcatcg gttgggaaga   1200

tactgacgct cttttgagac agttggctaa cgcagttaag gcaagaaggg gttgagaccc   1260

agctttcttg tacaaagtgg tc                                            1282
```